(12) United States Patent
Johnson et al.

(10) Patent No.: US 10,426,949 B2
(45) Date of Patent: Oct. 1, 2019

(54) SYSTEMS AND METHODS FOR OPTIMIZING PROGRAMMING AND USE OF NEUROMODULATION SYSTEMS

(71) Applicant: REGENTS OF THE UNIVERSITY OF MINNESOTA, Minneapolis, MN (US)

(72) Inventors: Matthew D. Johnson, North Oaks, MN (US); Edgar Peña, Minneapolis, MN (US); Simeng Zhang, Minneapolis, MN (US); Steven Deyo, Apple Valley, MN (US); YiZi Xiao, Eden Prairie, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 145 days.

(21) Appl. No.: 15/794,333

(22) Filed: Oct. 26, 2017

(65) Prior Publication Data

US 2018/0110973 A1  Apr. 26, 2018

Related U.S. Application Data

(60) Provisional application No. 62/412,996, filed on Oct. 26, 2016.

(51) Int. Cl.
*A61N 1/00* (2006.01)
*A61N 1/05* (2006.01)
(Continued)

(52) U.S. Cl.
CPC ............ *A61N 1/0534* (2013.01); *A61B 5/055* (2013.01); *A61B 5/4064* (2013.01);
(Continued)

(58) Field of Classification Search
CPC ............ A61N 1/36082; A61N 1/36096; A61N 1/36067; A61N 1/36128; A61N 1/36064;
(Continued)

(56) References Cited

U.S. PATENT DOCUMENTS

| | | | |
|---|---|---|---|
| 4,432,360 A | 2/1984 | Mumford | |
| 5,443,486 A | 8/1995 | Hrdlicka | |

(Continued)

FOREIGN PATENT DOCUMENTS

| | | |
|---|---|---|
| WO | WO 2004/096349 | 11/2004 |
| WO | WO 2005/028022 | 3/2005 |

(Continued)

OTHER PUBLICATIONS

Barbas et al., *Toward Patient-Specific Targeting and Parameter Setting of Deep Brain Stimulation for Relief of Depression*, Biol Phychiatry © 2014, pp. 914-196, available at http://dx.doi.org/10.1016/j.biopsych.2014.09.012.

(Continued)

*Primary Examiner* — Scott M. Getzow
(74) *Attorney, Agent, or Firm* — Patterson Thuente Pedersen, P.A.

(57) ABSTRACT

Systems and methods for programming multi-electrode neuromodulation systems, with applications for at least deep brain stimulation (DBS) therapy. One or more configurations can be generated and presented to a user for selection. The selected configurations can be settings for programming a pulse generator. The one or more configurations can be Pareto optimal in terms of one or more objective values and can be generated using a particle swarm optimization. The generated configurations can be visualized on a Pareto front for user selection. Objective values can include minimizing power use, maximizing activation of neural pathways and/or regions of interest, minimizing activation of neural path- (Continued)

ways and or regions of avoidance, and maximizing or minimizing the distance to sources of sensed functional data.

20 Claims, 13 Drawing Sheets

(51) Int. Cl.
  *A61N 1/36* (2006.01)
  *A61B 5/055* (2006.01)
  *A61N 1/372* (2006.01)
  *A61B 5/00* (2006.01)

(52) U.S. Cl.
  CPC ........ *A61B 5/4836* (2013.01); *A61N 1/36082* (2013.01); *A61N 1/36128* (2013.01); *A61N 1/37247* (2013.01)

(58) Field of Classification Search
  CPC ............ A61N 1/36185; A61N 1/36182; A61B 5/0042; A61B 5/0476; A61B 5/4064; A61B 5/4082–4094; A61B 5/4836; A61B 5/6868; A61B 5/7264; A61B 5/7235
  See application file for complete search history.

(56) References Cited

U.S. PATENT DOCUMENTS

| | | | |
|---|---|---|---|
| 5,713,922 | A | 2/1998 | King |
| 5,814,092 | A | 9/1998 | King |
| 6,463,328 | B1 | 10/2002 | John |
| 6,587,724 | B2 | 7/2003 | Mann |
| 6,622,048 | B1 | 9/2003 | Mann |
| 7,003,349 | B1 | 2/2006 | Anderson |
| 7,035,690 | B2 | 4/2006 | Goetz |
| 7,146,223 | B1 | 12/2006 | King |
| 7,177,674 | B2 | 2/2007 | Echauz |
| 7,181,286 | B2 | 2/2007 | Sieracki |
| 7,184,837 | B2 | 2/2007 | Goetz |
| 7,187,978 | B2 | 3/2007 | Malek |
| 7,209,787 | B2 | 4/2007 | DiLorenzo |
| 7,239,926 | B2 | 7/2007 | Goetz |
| 7,254,445 | B2 | 8/2007 | Law |
| 7,266,412 | B2 | 9/2007 | Stypulkowski |
| 7,305,268 | B2 | 12/2007 | Gilner |
| 7,346,382 | B2 | 3/2008 | McIntyre |
| 7,415,308 | B2 | 8/2008 | Gerber |
| 7,463,927 | B1 | 12/2008 | Chaouat |
| 7,463,928 | B2 | 12/2008 | Lee |
| 7,489,970 | B2 | 2/2009 | Lee |
| 7,519,431 | B2 | 4/2009 | Goetz |
| 7,548,786 | B2 | 6/2009 | Lee |
| 7,551,960 | B2 | 6/2009 | Forsberg |
| 7,657,319 | B2 | 2/2010 | Goetz |
| 7,676,273 | B2 | 3/2010 | Goetz |
| 7,680,526 | B2 | 3/2010 | McIntyre |
| 7,720,548 | B2 | 5/2010 | King |
| 7,801,618 | B2 | 9/2010 | Pless |
| 7,826,902 | B2 | 11/2010 | Stone |
| 7,860,548 | B2 | 12/2010 | McIntyre |
| 7,904,134 | B2 | 3/2011 | McIntyre |
| 7,957,809 | B2 | 6/2011 | Bourget |
| 8,090,446 | B2 | 1/2012 | Fowler |
| 8,121,694 | B2 | 2/2012 | Molnar |
| 8,180,451 | B2 | 5/2012 | Hickman |
| 8,180,601 | B2 | 5/2012 | Butson |
| 8,290,596 | B2 | 10/2012 | Wei |
| 8,326,433 | B2 | 12/2012 | Blum |
| 8,379,952 | B2 | 2/2013 | McIntyre |
| 8,483,836 | B2 | 7/2013 | Polefko |
| 8,538,543 | B2 | 9/2013 | McIntyre |
| 8,620,452 | B2 | 12/2013 | King |
| 8,644,946 | B2 | 2/2014 | Butson |
| 8,649,845 | B2 | 2/2014 | McIntyre |
| 8,649,872 | B2 | 2/2014 | Lee |
| 8,694,127 | B2 | 4/2014 | Pianca |
| 8,712,539 | B2 | 4/2014 | Goetz |
| 8,725,269 | B2 | 5/2014 | Nolan |
| 8,757,485 | B2 | 6/2014 | Drees |
| 8,781,592 | B2 | 7/2014 | Polefko |
| 8,805,518 | B2 | 8/2014 | King |
| 8,812,126 | B2 | 8/2014 | Butson |
| 8,838,242 | B2 | 9/2014 | Goetz |
| 8,914,121 | B2 | 12/2014 | Moffitt |
| 9,101,276 | B2 | 8/2015 | Georgopoulos |
| 2004/0199216 | A1 | 10/2004 | Lee |
| 2004/0267330 | A1 | 12/2004 | Lee |
| 2005/0060001 | A1 | 3/2005 | Singhal |
| 2005/0203588 | A1 | 9/2005 | King |
| 2006/0217781 | A1 | 9/2006 | John |
| 2006/0235472 | A1 | 10/2006 | Goetz |
| 2007/0043268 | A1 | 2/2007 | Russell |
| 2007/0083104 | A1 | 4/2007 | Butson |
| 2007/0185544 | A1 | 8/2007 | Dawant |
| 2007/0203538 | A1 | 8/2007 | Stone |
| 2007/0203545 | A1 | 8/2007 | Stone |
| 2007/0244519 | A1 | 10/2007 | Keacher |
| 2008/0027514 | A1 | 1/2008 | DeMulling |
| 2008/0103552 | A1 | 5/2008 | Goetz |
| 2008/0208284 | A1 | 8/2008 | Rezai |
| 2008/0215118 | A1 | 9/2008 | Goetz |
| 2009/0082829 | A1 | 3/2009 | Panken |
| 2009/0105787 | A1 | 4/2009 | Kokones |
| 2009/0112281 | A1 | 4/2009 | Miyazawa |
| 2009/0118787 | A1 | 5/2009 | Moffitt |
| 2010/0228314 | A1 | 9/2010 | Goetz |
| 2011/0040351 | A1 | 2/2011 | Butson |
| 2011/0066407 | A1 | 3/2011 | Butson |
| 2011/0160796 | A1 | 6/2011 | Lane |
| 2011/0172737 | A1 | 7/2011 | Davis |
| 2011/0191275 | A1 | 8/2011 | Lujan |
| 2011/0264165 | A1 | 10/2011 | Molnar |
| 2011/0313268 | A1 | 12/2011 | Kokones |
| 2012/0016378 | A1 | 1/2012 | Pianca |
| 2012/0277828 | A1 | 11/2012 | O'Connor |
| 2013/0226261 | A1 | 8/2013 | Sparks |
| 2014/0350634 | A1 | 11/2014 | Grill |

FOREIGN PATENT DOCUMENTS

| | | |
|---|---|---|
| WO | WO 2007/102945 | 9/2007 |
| WO | WO2008/005513 | 1/2008 |
| WO | WO 2009/055207 | 4/2009 |
| WO | WO 2009/134475 | 11/2009 |
| WO | WO 2010/065888 | 6/2010 |
| WO | WO2011/094752 | 8/2011 |
| WO | WO 2013/162681 | 10/2013 |

OTHER PUBLICATIONS

Barbe et al., *Individualized Current-Shaping Reduces DBS-Induced Dysarthria in Patients with Essential Tremor*, © 2014, American Academy of Neurology, 7 pages.

Berenstein, *Current Steering and Current Focusing in Cochlear Implants: Comparison of Monopolar, Tripolar and Virtual Channel Electrode Configurations*, © 2008, pp. 250-260.

Buhlmann, *Modeling of a Segmented Electrode for Desychnronizing Deep Brain Stimulation*, Dec. 2011, vol. 4, Article 15, pp. 1-8.

Butson, Christopher, *Patient-Specific Analysis of the Volume of Tissue Activated During Deep Brain Stimulation*, NIH Public Access, Jan. 15, 2007, pp. 1-16.

Butson, Christopher, *Patient-Specific Analysis of the Volume of Tissue Activated During Deep Brain Stimulation*, NIH Public Access, Jan. 2008, pp. 1-16.

Butson, C.R., *StimExplorer: Deep Brain Stimulation Parameter Selection Software System*, © Springer-Verlag 2007, 97(2), pp. 569-574.

Butson, Christopher R., IEEE Trans Vis Comput Graph, *Evaluation of Interactive Visualization on Mobile Computing Platforms for Selection of Deep Brain Stimulation Parameters*, Jan. 2013, 19(1), pp. 108-117.

(56) References Cited

OTHER PUBLICATIONS

Chatuvedi, Ashutosh et al., *Patient-Specific Models of Deep Brain Stimulation: Influence of Field Model Complexity on Neural Activation Predictions*, Apr. 1, 2010, 3(2), 23 pages.

Chatuvedi, Ashutosh et al., *Current Steering to Activate Targeted Neural Pathways During Deep Brain Stimulation of the Subthalamic Region*, Jul. 2012, 5(3), 16 pages.

Chatuvedi, Ashutosh et al., *Artificial Neural Network Based Characterization of the Volume of Tissue Activated During Deep Brain Stimulation*, NIH Public Access, J. Neural Eng., Oct. 2013, 17 pages.

Choi, Charles T. M., IEEE, *Modeling Deep Brain Stimulation Based on Current Steering Scheme*, vol. 47, No. 5, May 2011, pp. 890-893.

Cicione, Rosemary, Visual Cortex Response to Paired Stimulation of Retina, *Spatiotemporal Interactions in the Visual Cortex Following Paired Electrical Stimulation of the Retina*, © 2014, vol. 55, No. 12, pp. 7726-7738.

Contarino, M. Fiorella et al., Research Gate, *Directional Steering—A Novel Approach to Deep Brain Stimulation*, Sep. 2014 and as retrieved on Oct. 2, 2018, 9 pages.

Dumm, Gerald, *Virtual Electrodes by Current Steering in Retinal Prostheses*, vol. 55, No. 12, Dec. 2014, available at https://iovs.arvojournals.org/pdfaccess.ashx?url=/data/journals/iovs/933678/, as retrieved on Oct. 3, 2018, pp. 8078-8085.

Firszt, Jill B et al., *Current Steering Creates Additional Pitch Percepts in Adult Cochlear Implant Recipients*, © 2007, Otology & Neurotolgy, Inc., pp. 629-636.

Frankemolle, Anneke M.M., Brain: A Journal of Neurology, Brain 2010: 133, *Reversing Cognitive-Motor Impairments in Parkinson's Disease Patients Using a Computational Modelling Approach to Deep Brain Stimulation Programming*, pp. 746-761.

Oxford University, Brain: A Journal of Neurology, *Steering Technology for Deep Brain Stimulation*, © 2014, pp. 1854-1862.

Horsager, Alan et al., Visual Psychophysics and Physiological Optics, *Spatiotemporal Interactions in Retinal Prosthesis Subjects*, Feb. 2010, Vo. 51, No. 2, pp. 1223-1233.

Hunka, Karen, Journal of Neuroscience Nursing, *Nursing Time to Program and Assess Deep Brain Stimulators in Movement Disorder Patients*, Aug. 2005, vol. 37, No. 4, pp. 204-210.

Jepson, Lauren H. et al., Neurobiology of Disease, *Spatially Patterned Electrical Stimulation to Enhance Resolution of Retinal Prostheses*, Apr. 2, 2014, 34(14), pp. 4871-4881.

Keane, Maureen, NIH Public Access, J. Neural Eng., *Improved Spatial Targeting with Directionally Segmented Deep Brain Stimulation Leads for Treating Essential Tremor*, Aug. 2012, 9(4), 18 pages.

Kumar, Rajeev, *Methods for Programming and Patient Management with Deep Brain Stimulation of the Globus Pallidus for the Treatment of Advanced Parkinson's Disease and Dystonia*, Movement Disorders, Mar. 28, 2002, 2 pages.

Kuncel, Alex M., Clin Ceurophysiol, Sep. 2008, *A Method to Estimate the Spatial Extent of Activation in Thalamic Deep Brain Stimulation*, Sep. 2008, 20 pages.

Coenen, V.A. et al., *Explaining Clinical Effects of Deep Brain Stimulation Through Simplified Target-Specific Modeling of the Volume of Activated Tissue*, AJNR 33, www.ajnr.org, 9 pages.

Martens H.C.F, Clinical Neurophysiology, *Spatial Steering of Deep Brain Stimulation Volumes Using a Novel Lead Design*, © 2010, 9 pages.

Mcintyre, Cameron C., Conf Proc IEEE Eng Med Biol., *Customizing Deep Brain Stimulation to the Patient Using Computational Models*, © 2009, 5 pages.

McIntyre, Cameron C., Clinical Neurophysiology, *Electric Field and Stimulating Influence Generated by Deep Brain Stimulation of the Subthatlamic Nucleus*, © 2004, 7 pages.

McIntyre, Cameron C. et al., $33^{rd}$ Annual International Conference of the IEEE EMBS, *Improving Postural Stability via Computational Modeling Approach to Deep Brain Stimulation Programming*, Aug. 30 through Sep. 3, 2011, 2 pages.

Miocinvoic, Svjetlana, Parkinsonism and Related Disorders, Elservier, *Outcomes, Management and Potential Mechanisms of Interleaving Deep Brain Stimulation Settings*, 2014, 4 pages.

Montgomery Jr, E.B., *Deep brain stimulation programming: principles and practice*, 2010: Oxford University Press, 201 pages.

Moro, Elena, *Subthalaic Nucleus Stimulation: Improvements in Outcome with Reprogramming*, American Medical Association, © 2006, pp. 1266-1272.

Opie, N.L. et al., $35^{th}$ Annual International Conference of the IEEE EMBS, *Current Steering for High Resolution Retinal Implants*, © 2013, Jul. 3-7, 2013, 5 pages.

Kuncel, Alexis M., *Selection of Stimulus Parameters for Deep Brain Stimulation*, Science Direct, vol. 115, Issue 11, Nov. 2004, pp. 2431-2441.

Phibbs, Fenna T. et al., *Use of Efficacy Probability Maps for the Post-Operative Programming of Deep Brain Stimulation in Essential Tremor*, Parkinsonism Relat Disord, Dec. 2014, 11 pages.

Pollo Claudio et al., BRAIN: A Journal of Neurology, *Directional Deep Brain Stimulation: An Intraoperative Double-Blind Pilot Study*, 2015, 12 pages.

Bonham, Ben H. et al., Hear Res., *Current Focusing and Steering: Modeling, Physiology and Psychophysics*, Aug. 2008, 27 pages.

Schuurman, Rick et al., Stereotact Funct Neurosurg, *Papers Session—Stereotactic Technology*, May 29, 2013, 1 page.

Toader, Emil et al., $32^{nd}$ Annual International Conference of the IEEE EMBS, *Steering Deep Brain Stimulation Fields Using a High Resolution Electrode Array*, Aug. 31 through Sep. 4, 2010, 4 pages.

Townshend Brent, *Reduction of Electrical Interaction in Auditory Prostheses*, IEEE Transactions on Biomedical Engineering, vol. BME-34, No. 11, Nov. 1987, pp. 891-897.

Veraart, Claude, *Selective Control of Muscle Activation with a Multipolar Nerve Cuff Electrode*, IEEE Transactions on Biomedical Engineering, vol. 40, No. 7, Jul. 1993, pp. 640-653.

Volkmann, Jens et al., *Introduction to the Programming of Deep Brain Stimulators*, Movement Disorders, vol. 17, Suppl. 3, 2002, pp. S181-S187.

Volkmann, Jens, *Basic Algorithms for the Programming of Deep Brain Stimulation in Parkinson's Disease*, Movement Disorders, vol. 21, Issue S514, Jun. 29, 2006.

Xiao-Jiang, Feng, *Optimal Deep Brain Stimulation of the Subthalamic Nucelus—A Computational Study*, Journal of Computational Neuroscience, Dec. 2007.

Application and File History for U.S. Appl. No. 15/291,628, filed Oct. 12, 2016, Inventors: Xiao et al.

Xiao et al., *Theoretical Optimization of Stimulation Strategies for a Directionally Segmented Deep Brain Stimulation Electrode Array*. IEEE Trans Biomed Eng., Dated Feb. 2016, 31 pages.

Peña et al., *Particle Swarm Optimization for Programming Deep Brain Stimulation Arrays*, J Neural Eng. Feb. 2017;14(1):016014 (26 pages).

Johnson et al., *Advancing Deep Brain Stimulation Therapy Through Algorithms and Arrays* (presented at the University of Minnesota Biomedical Engineering seminar on Oct. 26, 2015).

Zhang et al., *Particle Swarm Optimization (PSO) for Programming DBS Arrays* (presented at the Minnesota Neuromdulation Symposium on Apr. 15, 2016).

Zhang et al., *Particle Swarm Optimization for Programming DBS Arrays* (presented at the Retreat for Institute of Translational Neuroscience on Jan. 13, 2016).

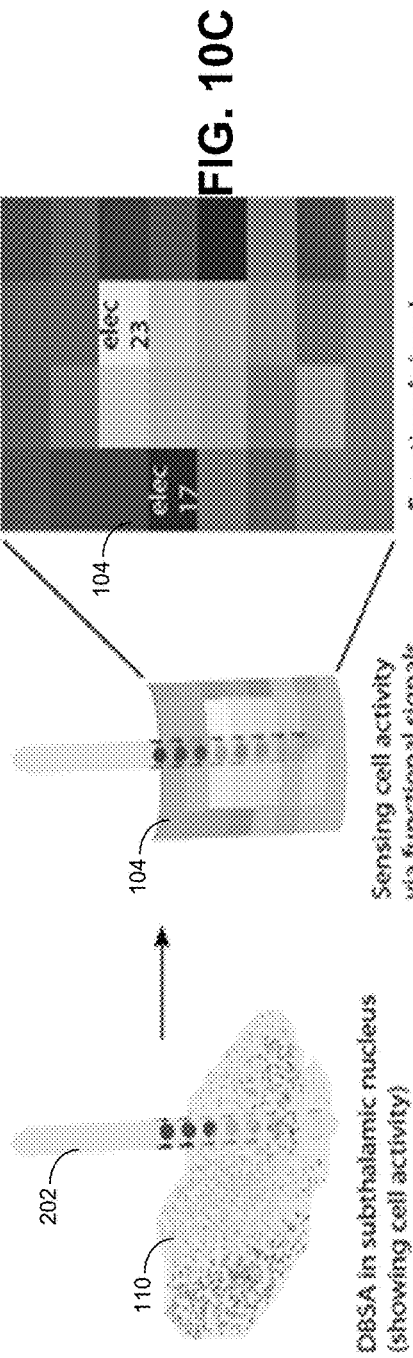
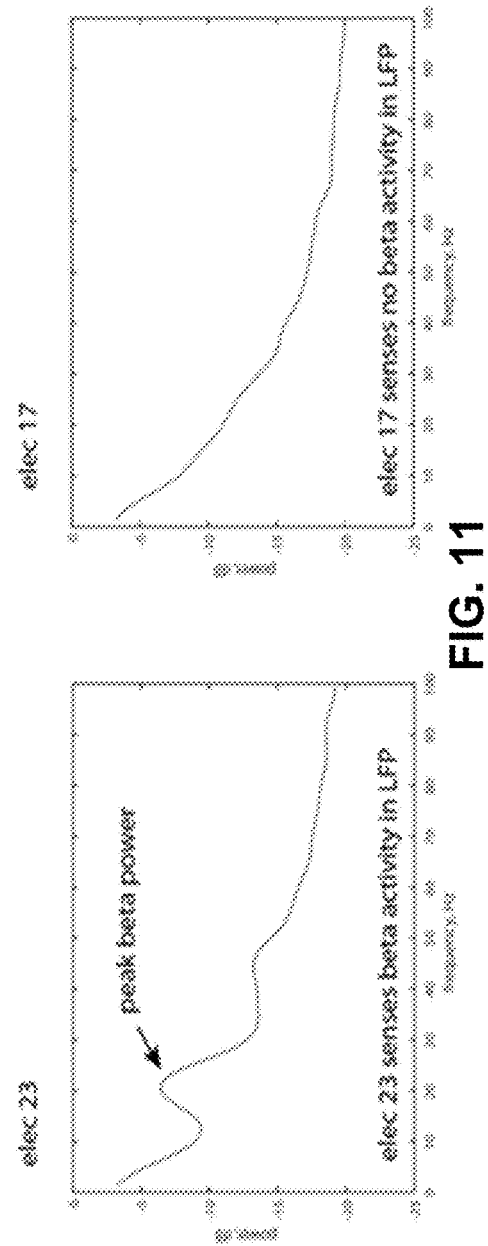
FIG. 10A
FIG. 10B
FIG. 10C
FIG. 11

Pareto front with electrode configurations (dots) given by one sample PSO run

Pareto front with electrode configurations (shaded dots) ranked by closeness to the source of functional signals. Lighter shades are less favorable electrode configurations and darker shades are more favorable configurations.

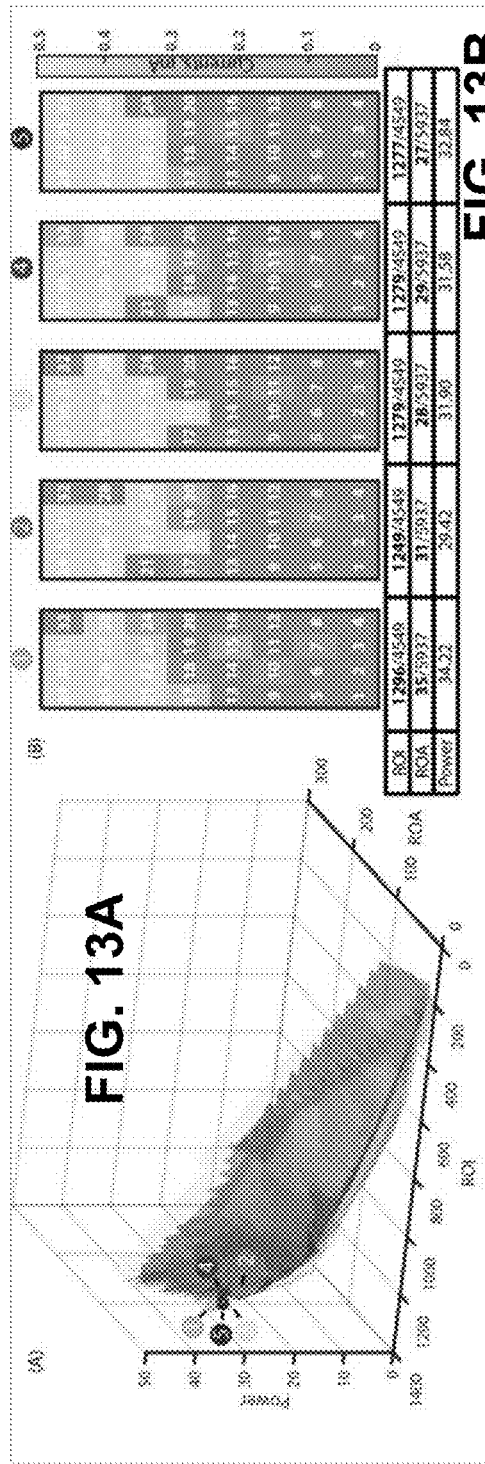
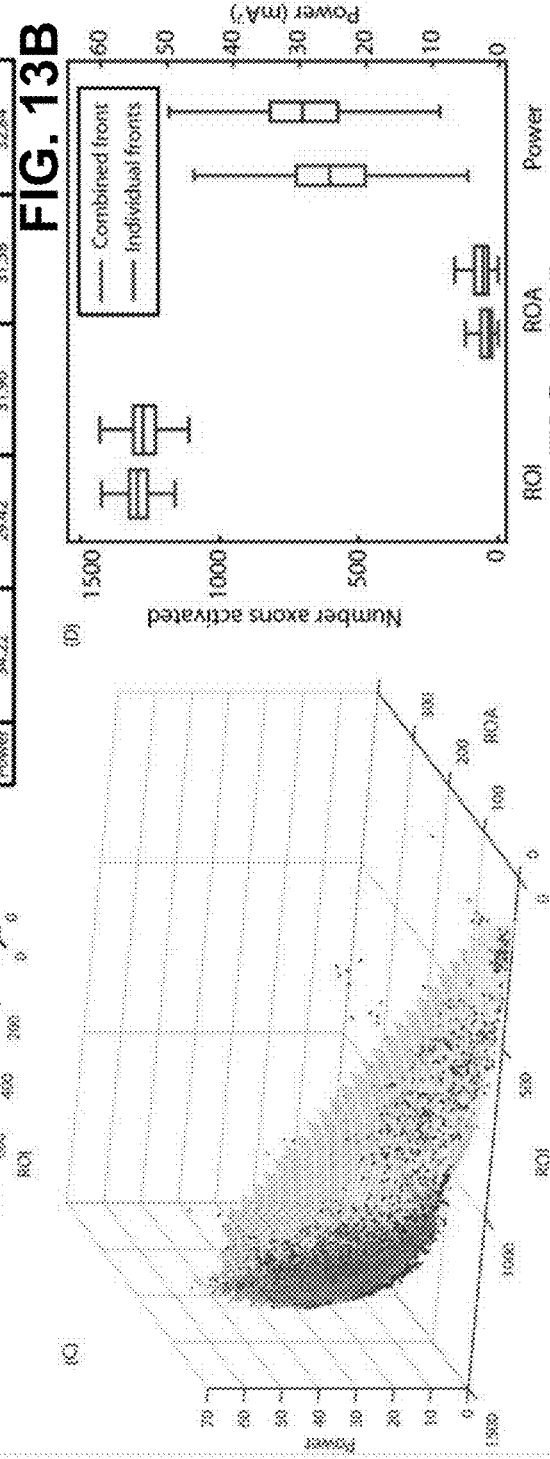
FIG. 13A
FIG. 13B
FIG. 13C
FIG. 13D

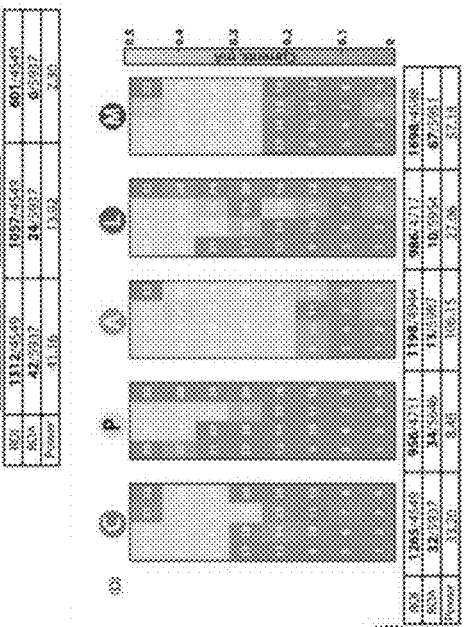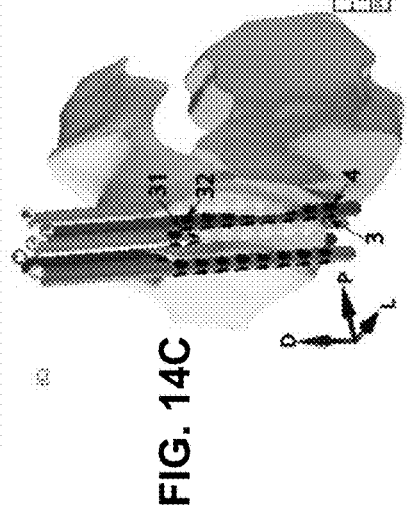
FIG. 14A
FIG. 14B
FIG. 14C
FIG. 14D

SYSTEMS AND METHODS FOR OPTIMIZING PROGRAMMING AND USE OF NEUROMODULATION SYSTEMS

RELATED APPLICATION

The present application claims the benefit of U.S. Provisional Application No. 62/412,996 filed Oct. 26, 2016, which is hereby incorporated herein in its entirety by reference.

STATEMENT REGARDING FEDERALLY SPONSORED RESEARCH OR DEVELOPMENT

This invention was made with government support under NS0924206 and NS081118 awarded by the National Institutes of Health. The government has certain rights in the invention.

TECHNICAL FIELD

The present disclosure relates generally to neurostimulation, and more particularly to systems and methods for determining configurations for deep brain stimulation therapy.

BACKGROUND

Deep brain stimulation (DBS) is an effective neurosurgical procedure for the treatment of neurological and neuropsychiatric disorders. The procedure involves placing one or more leads of electrodes into the brain to modulate pathological activity patterns with various forms of electrical stimulation. Successful treatment can be characterized by both symptom suppression and lack of stimulation-induced side effects. Such success requires accurate DBS lead placement as well as spatially targeted stimulation settings to avoid activating neural regions or pathways that induce, for example, adverse motor, sensory, and/or cognitive side effects for the patient.

Conventional designs of DBS leads (for example, the Medtronic Model 3387/3389) use four cylindrical electrodes to deliver current in an omnidirectional manner around the lead. An improvement to this design is to enable the steering of current delivery through electrodes segmented both along and around the DBS lead. Such DBS arrays (DBSAs) are especially useful in cases of imprecise implantation of DBS leads and for small or complex-shaped brain targets that are surrounded by regions and axonal fiber tracts that can elicit side effects when stimulated. However, with a higher number of electrodes available for stimulation, identifying therapeutic stimulation settings through trial-and-error programming is not readily feasible in a clinical setting.

Conventional programming of DBS settings works much like an optometrist performing a vision examination. A clinician will manually test many stimulation settings and evaluate the patient's response to each in order to determine the best one to use. This process can take hours within a single clinical visit and often several clinical visits over the course of weeks to months to optimize. There is a need for efficient, effective, and safe methods of operating, controlling, and/or programming DBSA settings, as conventional approaches to programming DBSAs have numerous drawbacks.

Conventional feedback-based systems for programming DBS settings have embedded technology to log and analyze patient response information or certain biomarkers (such as features in brain waves) in order to inform and update stimulation configurations. Sometimes a rating/ranking system is in place to determine the best configuration based on these responses/biomarkers.

Conventional brain mapping has been used by some researchers who have compiled intraoperative microelectrode stimulation data and mapped them onto a human brain atlas. An efficacy probability map is thus created by assigning each location on the brain atlas a probability for delivering therapeutic stimulation. The probability assignment is based on overlapping spatial distributions with therapeutic stimulation sites at the center of each distribution. Finally, the efficacy probability map (brain atlas) is nonlinearly warped onto the patient's MRI and used to determine the electrode settings that may deliver the best therapy. This approach is entirely based on empirical patient data.

Conventional patient anatomy-based computational neuron models can be used to predict the best stimulating electrode settings for modulating a particular pathway or pathways within the brain. A therapeutic target volume or pathway in the brain is segmented and reconstructed from the patient's MRI data. The volume is populated with simulated model biophysical neurons or grid coordinates and virtual stimulation is applied to them. The tissue enclosed, or pathways encompassed, by the activated volume under virtual DBS provide seed points to then understand the network of modulated brain regions. Large numbers of simulations are run in order to account for the different stimulating electrode configurations, neuron types and orientations, as well as relative locations between electrodes and neurons. The solutions for each simulation are stored in a large lookup table. Given a new target volume for stimulation, the pre-compiled database can be searched for the setting that gives the most overlap between the solution and the target volume.

A previous proposal, disclosed in co-owned U.S. patent application Ser. No. 15/291,628 to Xiao et al. (filed Oct. 12, 2016), includes a programming approach that identifies the electrode configuration that maximizes the overall likelihood that a region or pathway of interest will be activated. This is done by determining the theoretical maximum limits of excitatory influence at each location in a target volume and then tailoring the stimulation setting to try to achieve maximal proximity to that limit. Convex optimization is an efficient approach that can be used to identify the single best electrode configuration that maximizes likelihood of activation. The disclosure of U.S. patent application Ser. No. 15/291,628 is incorporated by reference herein in its entirety.

Conventional approaches for programming DBS systems cannot scale well to DBSAs with more than a handful of electrodes. Manual and feedback-based programming methods can be tailored to the patient but can take too much time and resources to implement effectively. Mapping methods are limited by the availability of a sufficiently rich source database and do not take the unique structure of a patient's brain tissue into account. Many conventional computational models require vast computational resources that may not be present in a clinical setting. Other, more computationally efficient methods that rely on convex optimization are limited by the assumption that a single optimal solution exists.

The need exists, therefore, for improved methods and systems for programming DBS systems.

SUMMARY

Embodiments of the present disclosure include systems and methods using particle swarm optimization (PSO) to provide clinicians with an intuitive, semi-automated approach for programming multi-electrode neuromodulation systems, with applications for neuromodulation therapy, (including deep brain stimulation (DBS) therapy). The disclosed system and methods produce a range of solutions of stimulation configurations that can achieve a plurality of objectives. In embodiments, target objectives can include maximizing neural activation of a neural pathways of interest, minimizing activation of neural pathways where stimulation is not desired, minimizing battery power consumption, and maximizing or minimizing the distance to sources of sensed functional data. The range of solutions computed can be subsequently presented visually to the clinician or other user, enabling the user to intuitively select a stimulation setting that matches desired activation outcomes.

A method for programming a pulse generator with a configuration for a deep brain stimulation array including one or more electrodes, the configuration including a stimulation setting for each electrode in the deep brain stimulation array, can comprise identifying one or more grid points representing a target tissue to be activated by stimulation through the one or more electrodes, identifying, for example, by receiving from the user, one or more objective values that are calculable based on the one or more grid points and a configuration to be balanced, generating one or more Pareto optimal configurations, presenting the one or more configurations to a user, receiving from the user a selected one of the one or more configurations, and providing, to a pulse generator capable of delivering therapy via each of the one or more electrodes, the selected configuration. The generated configurations can be Pareto optimal with respect to the objective values, such that no generated configuration is Pareto dominated by any other.

The configuration can be generated by initializing a search by storing data elements representing one or more particles, each particle having a current configuration and a local leader configuration in a memory, and allocating storage space for a set of dominant particles, and then iteratively performing the search.

The iterative search can comprise, for each iteration, calculating the one or more objective values for each of the one or more particles based on the one or more grid points and the current configuration for the particle, updating the set of dominant particles to contain only Pareto dominant particles, wherein a particle is Pareto dominant if it has at least one objective value that is better than the corresponding objective value of all other particles, determining the local leader configuration for each particle, determining a global leader configuration, and modifying the current configuration for each particle based on the local leader configuration for the particle and the global leader configuration until a termination criterion has been met. In embodiments, the termination criteria are selected from the group consisting of: a maximum number of iterations, convergence, and stalling. After the search completes, the configurations of each particle in the set of dominant particles can be provided.

The current configuration for each particle can be modified by modifying the current configuration for the particle based on an inertial component, a cognitive component, and a social component. In embodiments, the inertial component is based on the current and previous configurations for the particle, the cognitive component is based on the local leader configuration for the particle, and the social component is based on the global leader configuration. In embodiments one or more weighting factors can be applied while modifying the current configuration for each particle.

In embodiments, the local and global leader configurations can be determined by a hybrid approach using both Pareto and objective function optimization approach. An objective function calculable based on the one or more objective values can be identified or received from a user. The local leader configuration can be determined by calculating the objective function for the current configuration for the particle, and identifying the current configuration for the particle as the local leader configuration for the particle if the objective function for the current configuration is better than the objective function for a previous local leader configuration. The global leader configuration can by identified by identifying the particle having the local leader configuration with the best objective function value.

In embodiments, the local and global leader configurations can be determined by a purely Pareto dominance-based approach. Each particle can further comprise a local dominant set of configurations (i.e. a local Pareto front). When the objective values for the particles are calculated, the local dominant set of configurations can be updated to ensure that the local Pareto front contains only Pareto optimal solutions. For example, the current configuration can be added to the local dominant set of configurations if at least one of its objective values is better than the corresponding objective values of every other dominant set of configurations. In addition, any configuration can be removed if it there exists a configuration that is better in all objective values.

In embodiments, the local leader configuration for each of the one or more particles can be determined by choosing a random configuration from the local dominant set of configurations. The global leader configuration comprises choosing the local leader configuration for a random particle.

The objective values can be selected from the group including: a number of axons activated in one or more regions of interest, a number of axons activated in one or more pathways of interest, a number of axons activated in one or more regions of avoidance, a number of axons activated in one or more pathways of avoidance, and a total power required for stimulation.

Functional data related to the proximity of brain activity to each of the one or more electrodes can be received, and at least one of the objective values can include the proximity of brain activity to each of the electrodes activated by the configuration. In embodiments, the functional data can comprise spectral features of local field potential activity collected adjacent or distal to the stimulated electrodes.

A system for stimulation of brain tissue via an implantable deep brain stimulation array including one or more electrodes can comprise a pulse generator and pulse generator programming device including a brain geometry engine configured to generate, from brain geometry data, one or more grid points representing a target tissue to be activated, a discretization engine configured to determine an estimated modulation at each of the one or more grid points for a given configuration based on lead geometry data, and an optimization engine configured to generate one or more configurations, each configuration including a stimulation setting for each electrode.

The pulse generator programming device can further comprise a user interface engine configured to provide a display of the generated configurations to the user, and to receive from the user a selected configuration.

The pulse generator can be in data communication with the pulse generator programming device and be electrically coupled to the implantable deep brain stimulation array. The pulse generator can comprise a memory configured to store the selected configuration and a stimulation engine configured to deliver therapeutic pulses to each of the one or more electrodes according to the stimulation setting for the electrode in the configuration.

The pulse generator can further comprise a sensing engine configured to detect functional data related to the proximity of each of the one or more electrodes to brain activity, and at least one of the objective values can include the distance of brain activity to each of the electrodes activated by the configuration.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 10A is schematic view depicting a lead implanted in tissue, according to an embodiment.

FIG. 10B is schematic view depicting a visualization of functional signals at electrodes, according to an embodiment.

FIG. 10C is schematic view depicting a visualization of functional signals at electrodes, according to an embodiment.

FIG. 11 is a view of charts depicting functional signals at electrodes, according to an embodiment.

FIG. 13A is a graph depicting a visualization of a set of optimal stimulation settings from multiple executions of an optimization method, according to an embodiment.

FIG. 13B is a chart depicting electrode configurations at a set of optimal stimulation settings from multiple executions of an optimization method.

FIG. 13C is a graph depicting a visualization of a set of optimal stimulation settings from multiple executions of an optimization method, according to an embodiment.

FIG. 13D is a graph depicting consistency of solutions across multiple executions of an optimization method, according to an embodiment.

FIG. 14A is a chart depicting electrode configurations at a set of optimal stimulation settings including multiple disabled electrodes, according to an embodiment.

FIG. 14B is a chart depicting electrode configurations at a set of optimal stimulation settings including various current constraints, according to an embodiment.

FIG. 14C is a perspective view of multiple lead positions within tissue, according to an embodiment.

FIG. 14D is a chart depicting electrode configurations at a set of optimal stimulation settings for the lead positions of FIG. 14C, according to an embodiment.

Figure 1:
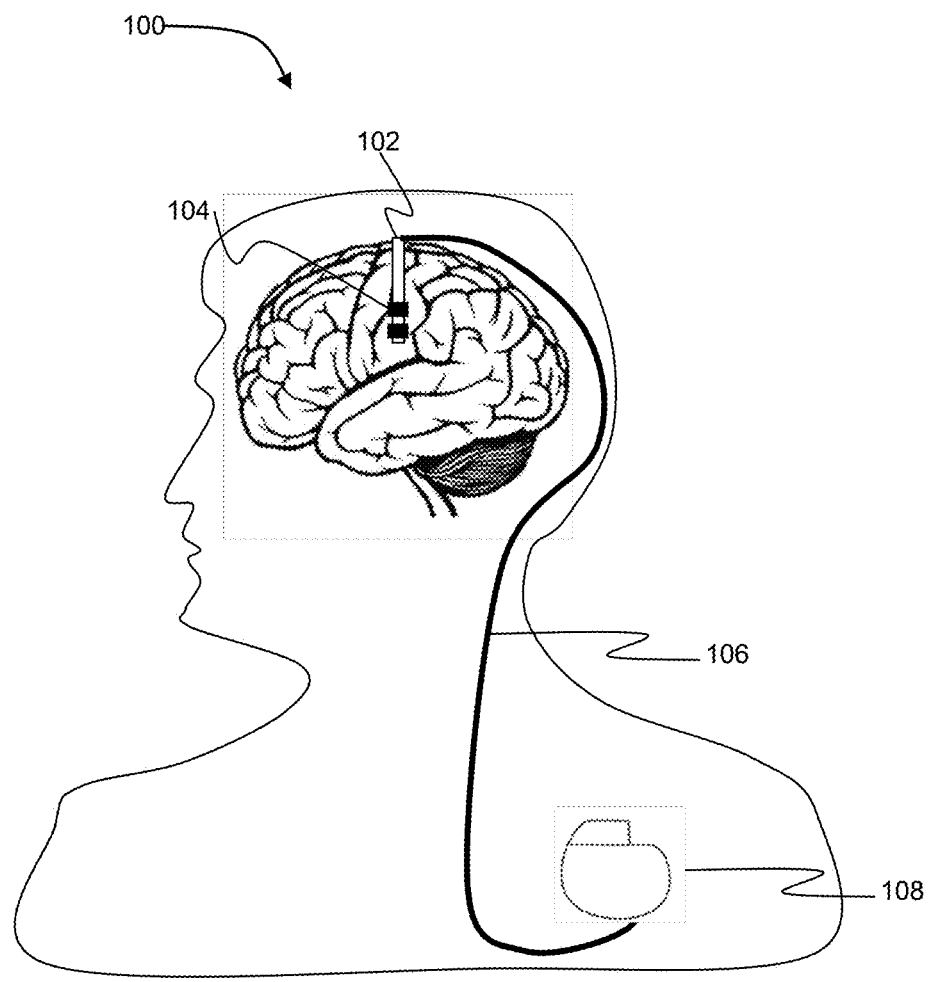
FIG. 1 is a schematic side view depicting a deep brain stimulation system implanted into the body of a patient, according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

FIG. 1 depicts an exemplary DBS system 100 including a lead 102 comprising one or more electrodes 104 implanted within the brain of a patient. Lead 102 is in electrical connection via an optional extension 106 to a pulse generator 108. In embodiments, pulse generator 108 can be implanted or external, and DBS lead 102 can be targeted to any brain region or pathway.

Figure 2:
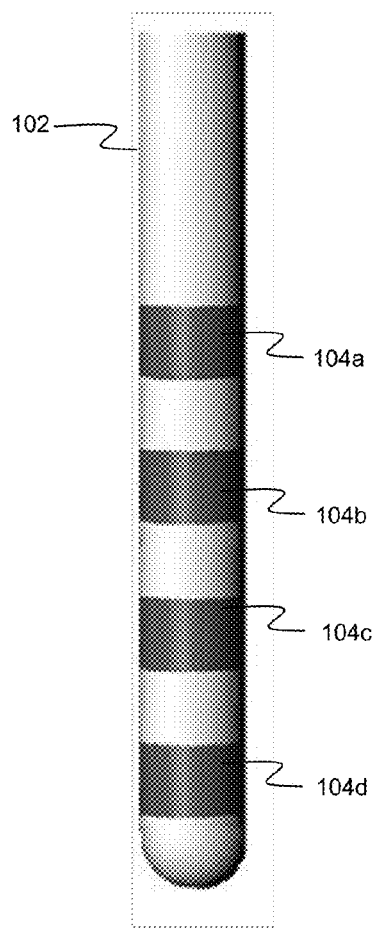
FIG. 2 is a perspective view depicting a portion of a deep brain stimulation lead with four electrodes, according to an embodiment.
Figure 3:
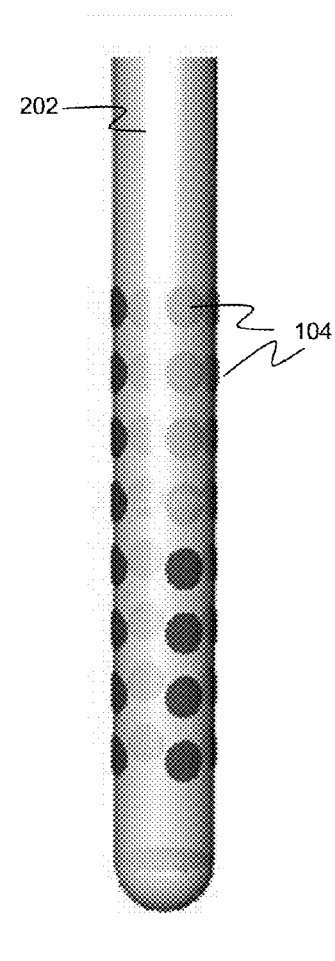
FIG. 3 is a perspective view depicting a portion of a deep brain stimulation lead with an array of electrodes, according to an embodiment.

FIG. 2 depicts a detailed view of lead 102 with four circumpolar electrodes 104a-d. FIG. 3 depicts a DBS array (DBSA) lead 202 with a greater number of electrodes 104 spaced radially around and transversely along lead 202. Leads 102 and 202 can include an insulating layer surrounding conductors (not shown) providing electrical connection from electrodes 104 to pulse generator 108. Leads 102 and 202 are examples of suitable leads, and other configurations, arrangements and types of leads can be used in various embodiments discussed herein.

Figure 4:
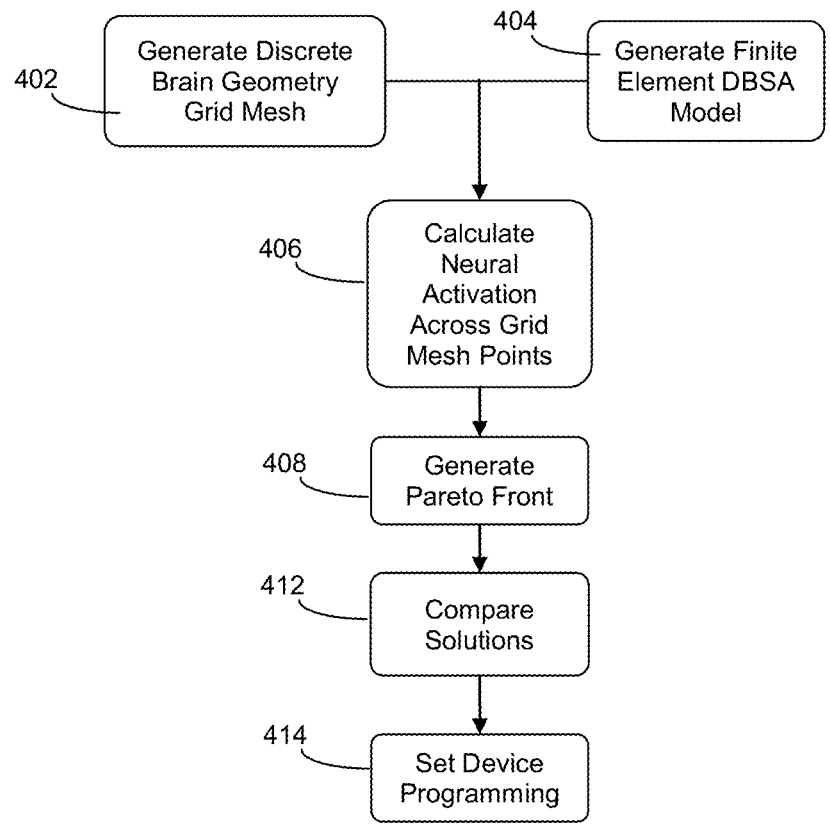
FIG. 4 is a flowchart depicting a method of generating stimulation settings for a deep brain stimulation array, according to an embodiment.

Embodiments of the present disclosure are directed to determining and providing therapies by electrical stimulation of one or more electrodes 104 by pulse generator 108. FIG. 4 is a flowchart of an overview of a method by which pulse generator 108 can be programmed with settings for each electrode that provide maximum stimulation to one or more target regions or pathway while minimizing stimulation of other regions or pathways. Though this will be discussed in more detail below, including in the context of examples of related systems, hardware and other features, the overview related to FIG. 4 can be helpful for appreciating various features individually and in combination.

At 402, brain geometry data unique to a specific patient (for example MRI data) can be combined with brain atlas data to generate a discrete brain geometry grid mesh. Data regarding the configuration of the electrodes 104 on the implanted lead 102 or 202 can be used to generate a finite element model of the electrode configuration at 404. At 406, predictions regarding axonal modulation at each of the grid points can be calculated and used to construct a Pareto front of Pareto optimal solutions. The solutions can be compared at 412, and device programming can be set and/or carried out at 414. In other embodiments, more or fewer activities can be carried out, such that additional activities not depicted in FIG. 4 can be included, or activities that are depicted can be omitted.

Figure 5:
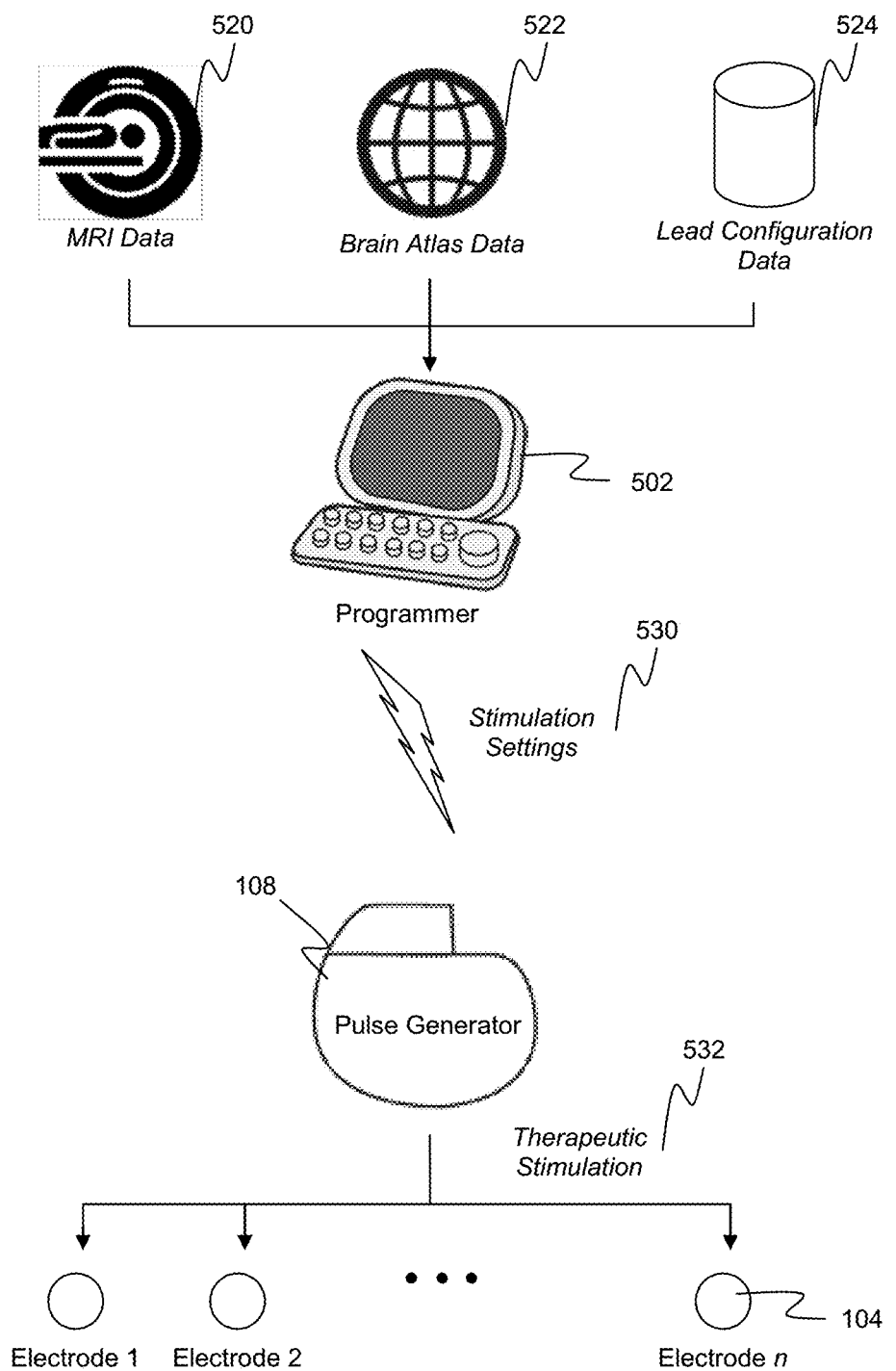
FIG. 5 is a block diagram depicting a schematic view of a deep brain stimulation system and a programmer, according to an embodiment.

Embodiments can include systems of hardware and software adapted to carrying out the activities depicted in FIG. 4 above. FIG. 5 depicts an example system in which MRI data 520, brain atlas data 522 and lead configuration data that includes placement and orientation of the lead within the brain volume 524 are used by a programmer device 502 and pulse generator 108 in order to provide programmed therapeutic stimulation 532 to electrodes 104. The data sources 520, 522, and 524 can be used by programmer device 502 to determine stimulation settings 530 that are customized to the patient. In various embodiments, all three data sources 520, 522, 524 can be used, or fewer than all three can be used. Programmer device 502 can be electrically and/or communicatively coupled to or otherwise receive data from some or all of data sources 520, 522, 524. Pulse generator 108 directs therapeutic stimulation currents 532 according to the stimulation settings 530, which can be determined by programmer device 502 based at least in part on the data from data sources 520, 522, 524. In still other embodiments, data from different or additional data sources also or instead can be communicated to programmer device 502 for consideration in determining stimulation settings 530.

Figure 6A:
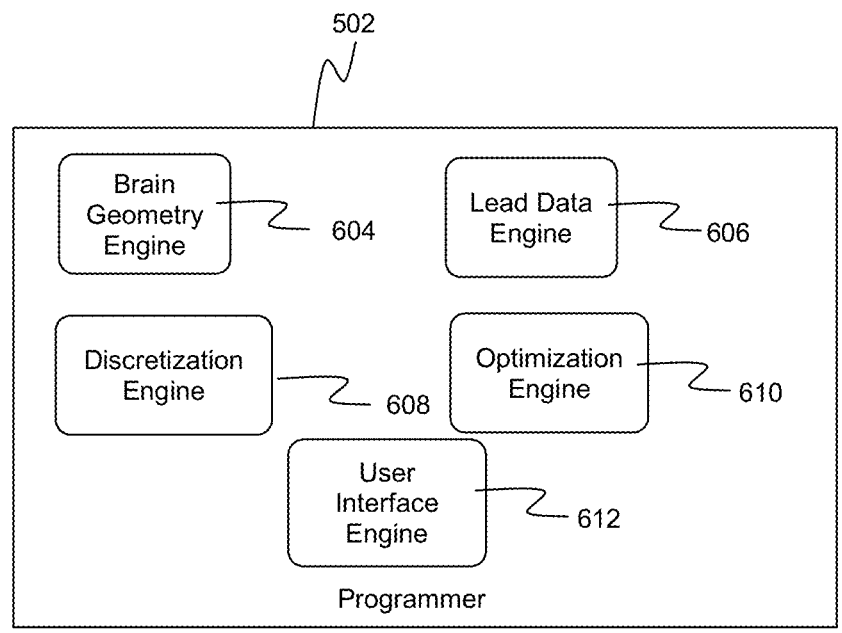
FIG. 6A is a block diagram depicting a schematic view of a programmer, according to an embodiment.

Pulse generator 108 is in wired or wireless communication with programmer device 502. Programmer device 502 can be a handheld device, laptop or desktop computer, server, tablet, cellular or smart phone or other computing device capable of data communication with pulse generator 108. Programmer device 502 can present a user interface adapted to allow a user, such as a clinician, patient, or researcher, to review, monitor, and update device data and settings. As can be seen in FIG. 6A, programmer device 502 can comprise a brain geometry engine 604, lead data engine 606, discretization engine 608, optimization engine 610, and user interface engine 612. Engines 604, 606, 608, 610, 612 can be software, firmware, hardware or combinations thereof in embodiments and can comprise or be controlled, executed and/or coupled by a processor, such as a microprocessor, or other computing device. In still other embodiments, engines 604, 606, 608, 610, 612 can be different functions, routines, algorithms, functional units, of a processor or other device. Examples of the tasks, activities and other characteristics of engines 604, 606, 608, 610, 612 are discussed below. Other components of programmer device 502, including hardware and software components, can be included but are not specifically depicted in FIG. 6A.

Figure 6B:
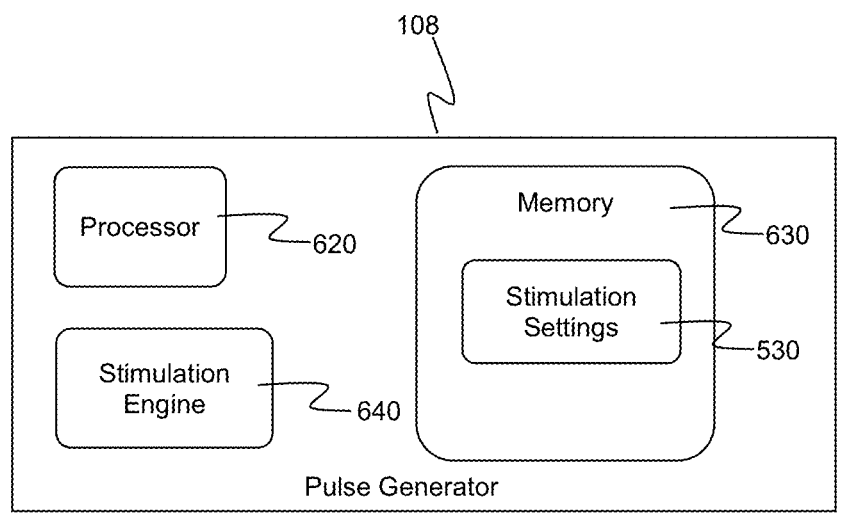
FIG. 6B a block diagram depicting a schematic view of a pulse generator, according to an embodiment.

As can be seen in FIG. 6B, pulse generator 108 can comprise a processor 620 and a memory 630. Memory 630 can include storage for stimulation settings 530 for each of electrodes 104 present on lead 102 or 202. Stimulation settings 530 can be, for example, an array, hash table, dictionary, database or other data structure keyed to each electrode 104. A set of stimulation settings 530 for each electrode 104 on lead 102 or 202 is a configuration. The value at each key can be the amount of current (for example, in milliamps) to be directed to each electrode 104 during a therapy pulse. Stimulation settings 530 can also include other data items such as pulse time, pulse interval, pulse pattern, or pulse waveform shape. Pulse generator 108 can also have a communication engine, capable of wired or wireless communication with programmer device 502. Pulse generator 108 can also have one or more sensing engines capable of interpreting data sensed by electrodes 104 or via sensors within pulse generator 108 itself. Pulse generator 108 can have a stimulation engine 640 capable of independent current-controlled stimulation through each electrode 104 provided. In embodiments, pulse generator 108 can house any of brain geometry engine 604, lead data engine 606, discretization engine 608, and optimization engine 610 instead of or in addition to the engines in programmer device 502.

In operation, pulse generator 108 can provide therapy to brain or other tissue by directing pulses of electrical current to each electrode 104 based on the values stored in stimulation settings 530. In order to determine optimum stimulation settings that maximize therapeutic value while minimizing side effects, patient and lead specific data can be combined by programmer device 502 in order to determine optimum stimulation settings 530.

Returning now to FIG. 6A, the various engines of programmer device 502 will be described in more detail. Each of the engines can be adapted to perform one or more of the activities of the method discussed regarding FIG. 4, for example.

Brain geometry engine 604 is adapted to receive brain geometry data and generate a three-dimensional (3D) grid of multiple layers corresponding to the tissue that is the target of stimulation (i.e., generate a discrete brain grid at 402 of FIG. 4). Brain geometry data can include MRI data 520 which can be produced via magnetic resonance imaging (MRI) of the patient. Embodiments of MRI data 520 can comprise of, for example, T2-weighted imaging or susceptibility weighted imaging (SWI).

Figure 7:
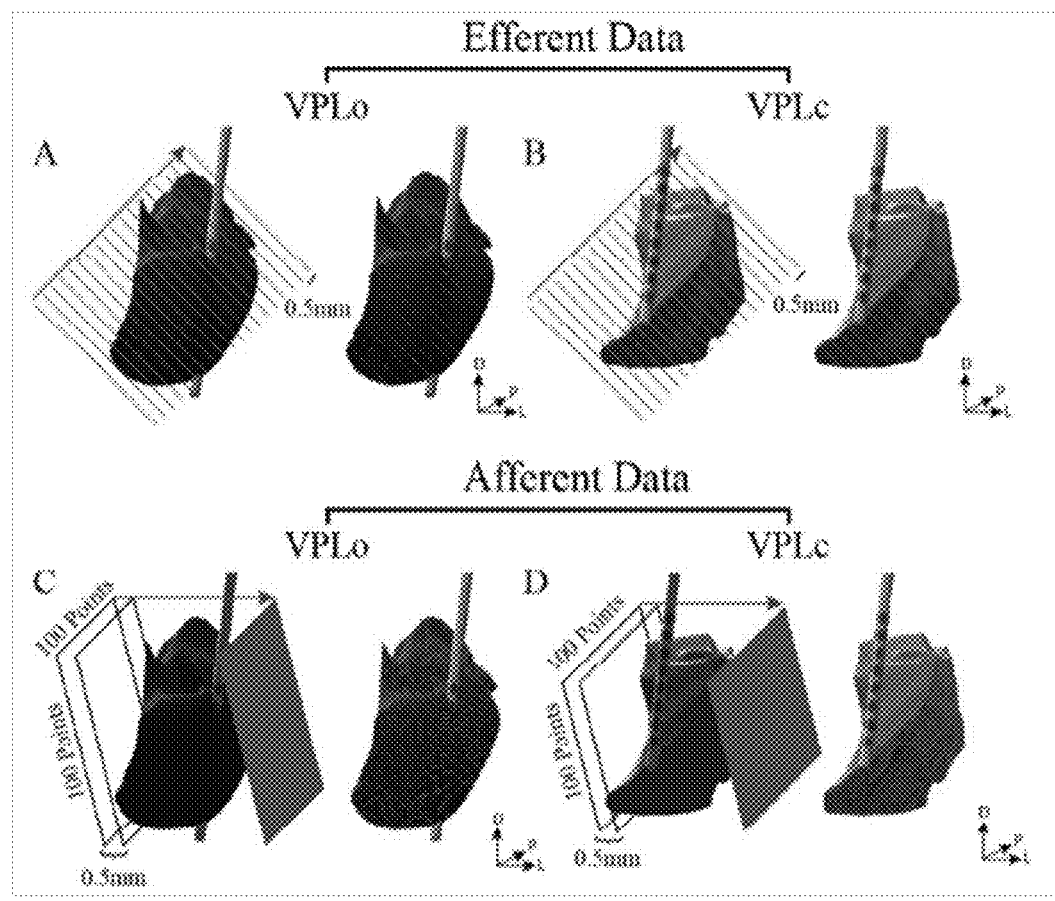
FIG. 7 is a simulated view of a discretized brain volume according to an embodiment.

In embodiments, brain geometry engine 604 then can obtain coronal images from the MRI data and use those images to contour the target tissue. Returning to the above example, brain geometry engine 604 can align the acquired SWI data to the anterior commissure (AC)-posterior commissure (PC) plane and slice it to produce serial coronal sections. These coronal sections, or images, can be analyzed to identify those that span the target tissue and matched to places from a tissue atlas (for example, a brain atlas 522) in order to extract the contours of the target tissue. Brain geometry engine 604 can then map the contours onto a 3D grid of axon nodal compartment locations (e.g., in both the afferent and efferent axonal fiber directions from thalamus) as can be seen in FIG. 7. This is just one example, however, and those skilled in the art will appreciate that other MRI data and acquisition sequences, as well as other mapping techniques including more detailed axonal tracings, can be used in other embodiments.

Lead data engine 606 is adapted to generate and store a finite element model (FEM) of the voltage distribution resulting from electrical stimulation through each of electrodes 104 on lead 102 or 202 (i.e., generate a finite element DBSA model at 404 of FIG. 4). The electrode surfaces can be designated as boundary current sources, and the walls of the bulk tissue cylinder can be set to ground. The voltage distributions resulting from electrical stimulation through the electrodes can be calculated, such as via the finite element method by solving Poisson's equation. Stimulation then can be performed for each electrode 104. In one embodiment, the stimulation comprises monopolar cathodic or anodic stimulation (e.g., at ±1 mA), with each of the electrodes individually stimulated as the cathode and then the anode (or vice-versa). Programmer device 502 can calculate the finite element model, or the calculated data can be provided to programmer device 502 by a user. Programmer device 502 can optionally store finite element models for multiple forms of leads 102 or 202.

Discretization engine 608 is configured to determine the estimated modulation for a given stimulation setting at each point in the grid produced by brain geometry engine 604 (for example at 406). In one embodiment, discretization engine 608 can first calculate an activating function (AF) at each grid point along the axonal fiber direction. This can be done, for example, using the following formula in one embodiment:

$$\frac{\partial^2 V}{\partial x^2} = \frac{V(x+\Delta x) - 2V(x) + V(x-\Delta x)}{\Delta x^2}$$

in which x is a position along the direction of the fibers, V is the voltage value as a function of position, and $\Delta x$ is the internodal distance. In other words, the AF is the second-order spatial difference of the voltage within the target tissue at each grid point.

In embodiments, a modified activating function (MAF) can be used to predict axonal activation. The MAF can be computed using the second spatial difference using extracellular potentials from non-adjacent nodes as in the following formula in one embodiment:

$$\text{MAF} = V(x+2\Delta x) - 2V(x) + V(x-2\Delta x)$$

Notably, this approach is fundamentally the same as the activating function, except that it yields a smoother version of the activating function. Because this modified spatial difference is a linear function of the extracellular potentials, the superposition principle can be used to efficiently predict MAF values for an arbitrary electrode configuration. For each axon, an N-by-M matrix (denoted as the "C matrix") is constructed containing the MAF value for all N nodes of Ranvier when stimulating through each electrode individually. This enables computing the MAF value at every node for arbitrary electrode configurations by multiplying the C matrix with the M-by-1 vector of currents going through each electrode of the DBSA.

These formulations for AF and MAF are just examples, however, and those skilled in the art will appreciate that choice of other formulations can be made in other embodiments. Notably, other functional derivatives can be used in place of AF or MAF to represent membrane polarization at the grid points. This can include, for example, a driving force function, incorporating extracellular potentials from additional nodes of Ranvier. Additionally, other embodiments can include, but are not limited to, solving for the full multi-compartment axon or neuron model equations as well as functions related to synaptic activation such as the first spatial difference equation. Embodiments can also include functions that incorporate multiple fiber directions. Axons that overlap spatially with the DBSA can also be discarded.

The AF or MAF values for the remaining n points can be stored in a matrix. In one embodiment, the matrix can comprise an m×n matrix C, where m is the total number electrodes, the $i^{th}$ row contains the AF or MAF values resulting from stimulation through the $i^{th}$ electrode alone, delivering −1 mA monopolar cathodic current. An example of matrix C is:

$$C = \begin{pmatrix} \nabla^2_{1,1} & \cdots & \nabla^2_{1,n} \\ \vdots & \ddots & \vdots \\ \nabla^2_{m,1} & \cdots & \nabla^2_{m,n} \end{pmatrix}$$

Poisson's equation in electrostatics dictates that voltage distribution is proportional to the current, $\nabla \cdot \sigma \nabla V = -I$, where $\sigma$ is the specific electrical conductivity of the tissue and I is the current. From this, it is possible to derive that the current changes with the second difference of the voltage. Therefore, it can be shown that the AF or MAF values resulting from multiple voltage sources can be linearly superimposed.

In embodiments, MAF values can be used to predict axonal activation. An axon can be considered activated if, for a given electrode configuration, the MAF value exceeds a predefined threshold (MAFT) at one or more of grid points that correspond to a node of the axon. Because the choice of MAFT is dependent on the specific axonal geometry, MAFT can be tuned empirically to maximize its predictive accuracy for the given geometry. In embodiments, a MAFT value can be determined by biophysical multi-compartment model simulation. In addition, other computational approaches for modeling axonal excitability resulting from DBSA may be used as long as the predictive functions are specified programmatically.

Assuming a single objective such as, for example, maximizing the total number of axons activated, stimulation settings 530 can include the electrode configuration that results in the highest number of predicted activated axons. In clinical settings however, multiple objectives may need to be balanced in order to determine stimulation settings 530 and set device programming at 414. Where each objective has a known importance, or "weight", a scalar objective function can be defined taking into account each weight. The value of this scalar objective function must then be calculated for each possible electrode configuration in order to determine an optimal electrode configuration.

In an example, objectives may include maximizing $R(\vec{x})$, the number of axons activated in a region of interest (ROI), minimizing $S(\vec{x})$, the number of axons activated in a region of avoidance (ROA), and minimizing $P(\vec{x})$, the power dissipated by the stimulator. In addition, minimizing $S(\vec{x})$ may be twice as important as maximizing $R(\vec{x})$, which is itself twice as important as minimizing $P(\vec{r})$. If these weights are known, the objective function may be defined as a summation, such as:

$$-R(\vec{x}) + (2)S(\vec{x}) + 0.5P(\vec{x})$$

Therefore, the optimal electrode configuration x is simply the one that minimizes the objective function value (given constraints on x).

In order for this linear-aggregation based approach to be universally applicable, however, the weighting factors cannot be fixed, since the importance of each objective may vary between patients and over time. Therefore, ideally, the optimization problem would be solved for every possible combination of weightings. If a clinician is to select which weighting combinations should be run and then run the algorithm for each individually, this can present an overwhelming set of parameters for a clinician to choose from.

In embodiments including an improved approach, optimization engine 610 can produce one or more Pareto optimal solutions for a plurality of objectives, such as at 408 in FIG. 4. In embodiments, parameter space exploration optimization algorithms such as particle swarm optimization can solve optimization problems through a series of searches through a solution space performed by a collection of interacting individuals, or particles. As used herein, "Pareto optimal" can refer to solutions that appear to be Pareto optimal, or are very close to actual Pareto optimal solutions.

Particle swarm optimization algorithms employ cognitive and social components that adapt across multiple iterations (or generations), much like genetic algorithms and other evolutionary algorithms. In the case of particle swarm optimization algorithms, the individuals (or particles) survive throughout all iterations and continue to refine the solution to the overall problem. This iterative refining process enables particle swarm optimization algorithms to efficiently and effectively search the solution space. For multi-objective particle swarm optimization algorithms, there are a number of approaches for selecting best, or "leader," solutions and subsequently updating particle positions. In embodiments, optimization engine 610 can use a mix between the linear aggregation-based approach and a Pareto dominance-based approach. In particular, embodiments can use a linear aggregation objective function to guide exploration of the particles, and use Pareto dominance criteria to construct an archive of Pareto optimal points from all explored candidate solutions. Other embodiments can use a fully Pareto dominance-based approach to guide exploration, consisting of objective vectors that are comprised of objective values, but not requiring an explicit objective function.

Figure 8A:
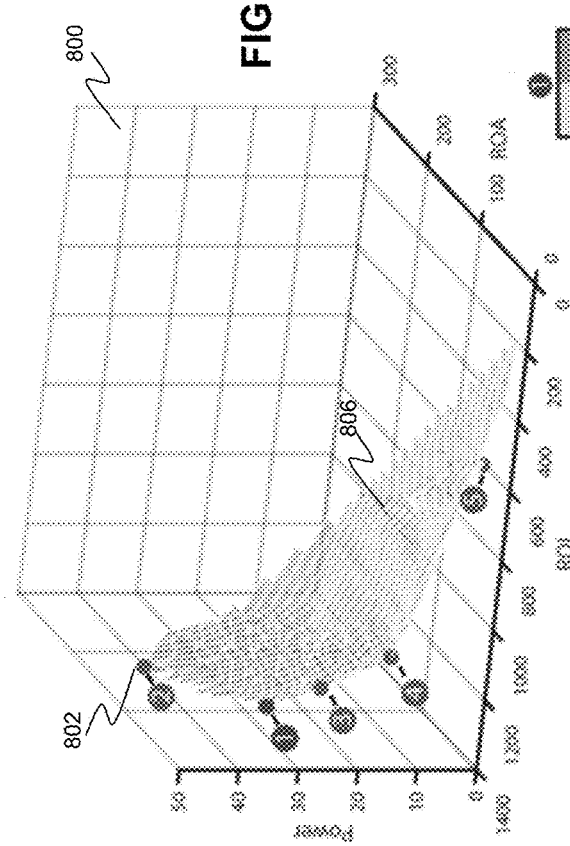
FIG. 8A is a graph depicting a visualization of a set of optimal configurations, according to an embodiment.
Figure 8B:
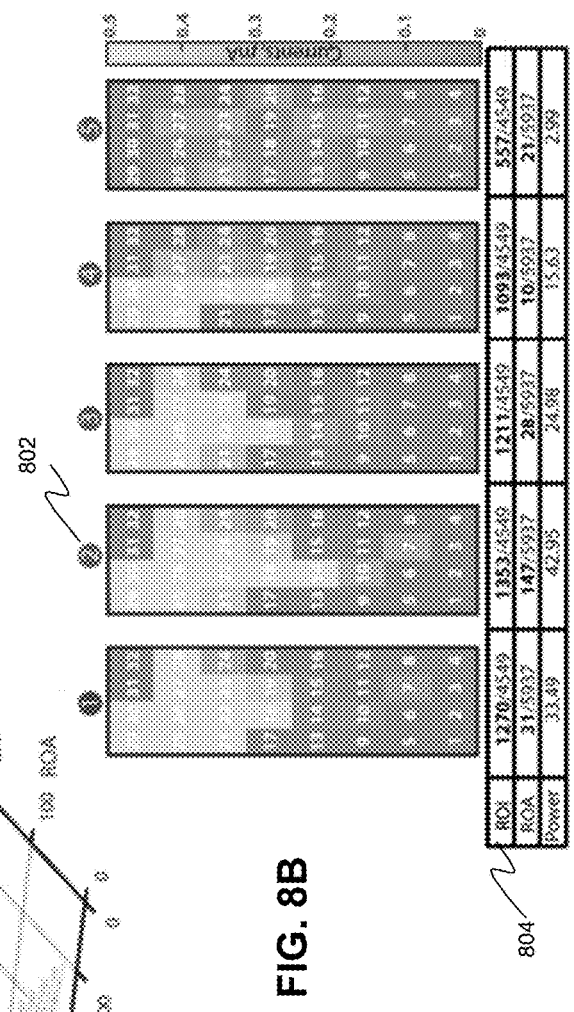
FIG. 8B is chart depicting electrode configurations at a set of optimal configurations, according to an embodiment.

FIG. 8A is a graph depicting an optimization problem space for electrode configurations based on an optimization problem involving three objectives, according to an embodiment. In embodiments, the optimization problem space 800 is a d-dimensional space in which d is the number of objectives to be optimized, and each point of that space corresponds to the coordinate values for each objective function. Each individual, or particle in optimization space 800, contains values representing a given electrode configuration (i.e. a vector x containing a current value for each electrode), and therefore corresponds to a point in the m-dimensional solution space (where m is the number of electrodes). FIG. 8B is a pictorial view of five example electrode configurations 802 (where lighter-colored rectangles are associated with higher current values), and the corresponding objective values 804. Each example electrode configuration 802 is also plotted within the optimization problem space 800 in FIG. 8A. Also depicted in FIG. 8A is a Pareto front 806 that represents a set of solutions that are each Pareto-optimal, given the associated tradeoffs. The Pareto front 806 can be presented to the user via user interface engine 612 to allow the user to readily select among multiple Pareto-optimal electrode configurations.

Figure 8C:
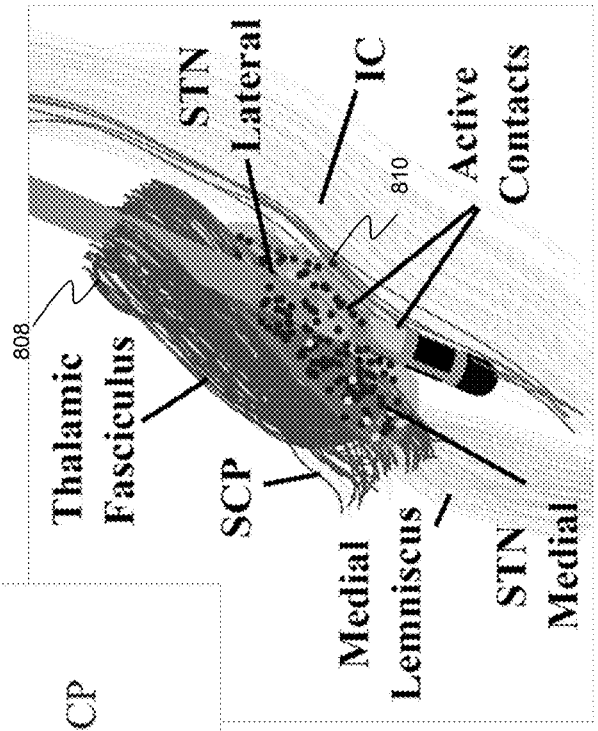
FIG. 8C is a graph depicting a visualization of a set of optimal configurations, according to an embodiment.

FIG. 8C is a graph depicting an optimization problem space 800' for electrode configurations based on an optimization problem involving seven objectives, according to an embodiment. While optimization problem space 800' and Pareto front 806' are depicted with only three dimensions, the optimization problem space 800' includes additional dimensions. In the depicted embodiment, the objective values are power, four regions and pathways of interest (the subthalamic nucleus (STN) lateral, the subthalamic nucleus medial, the thalamic fasciculus, and the superior cerebellar peduncle (SCP)), and two pathways of avoidance (the medial lemniscus (ML) and the internal capsule (IC)). The graph depicted in FIG. 8C depicts a three-dimensional view of the STN lateral, SCP, and IC axes. In embodiments, user interface engine 612 can enable the user to select a subset of optimization values to display when generating the depicted Pareto front.

Figure 8D:
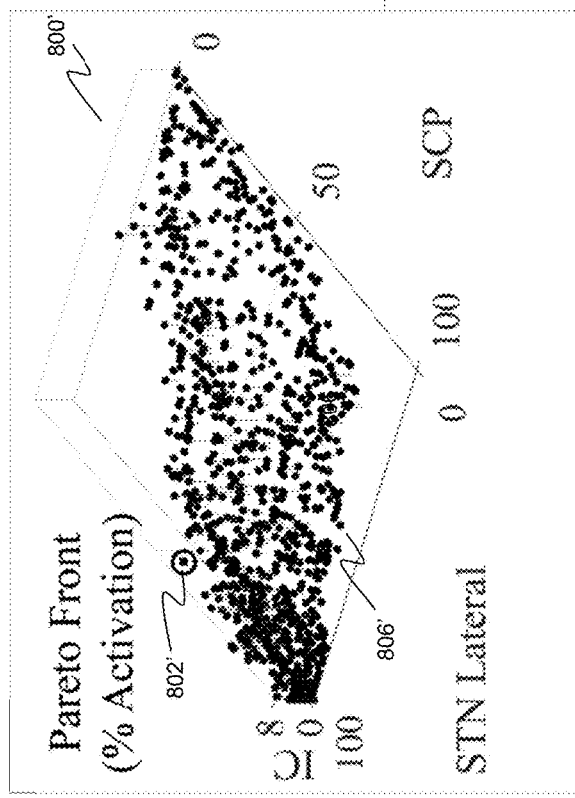
FIG. 8D is simulated view depicting a portion of a deep brain stimulation lead and activated tissue, according to an embodiment.

FIG. 8D is a pictorial view depicting a lead 202 in situ within a brain volume. The view depicted is color coded (in grayscale) based on the electrode configuration associated with the circled point 802' on Pareto front 806'. In the depicted example, the active electrodes 104 are indicated by a lighter color. In this case, the selected electrodes are the most proximal cylindrical contact and the anterior-facing directional contact. Activated fibers 808 are depicted with thicker and darker lines, and activated STN cells 810 are depicted with black dots.

As can be seen in FIG. 8D, the activation resulting from the configuration selected at 802' reflects little to no activation of ML and IC (the pathways of avoidance), high activation of STN lateral and medial (the regions of interest), and high activation of thalamic fasciculus and SCP (additional pathways of interest).

Figure 9:
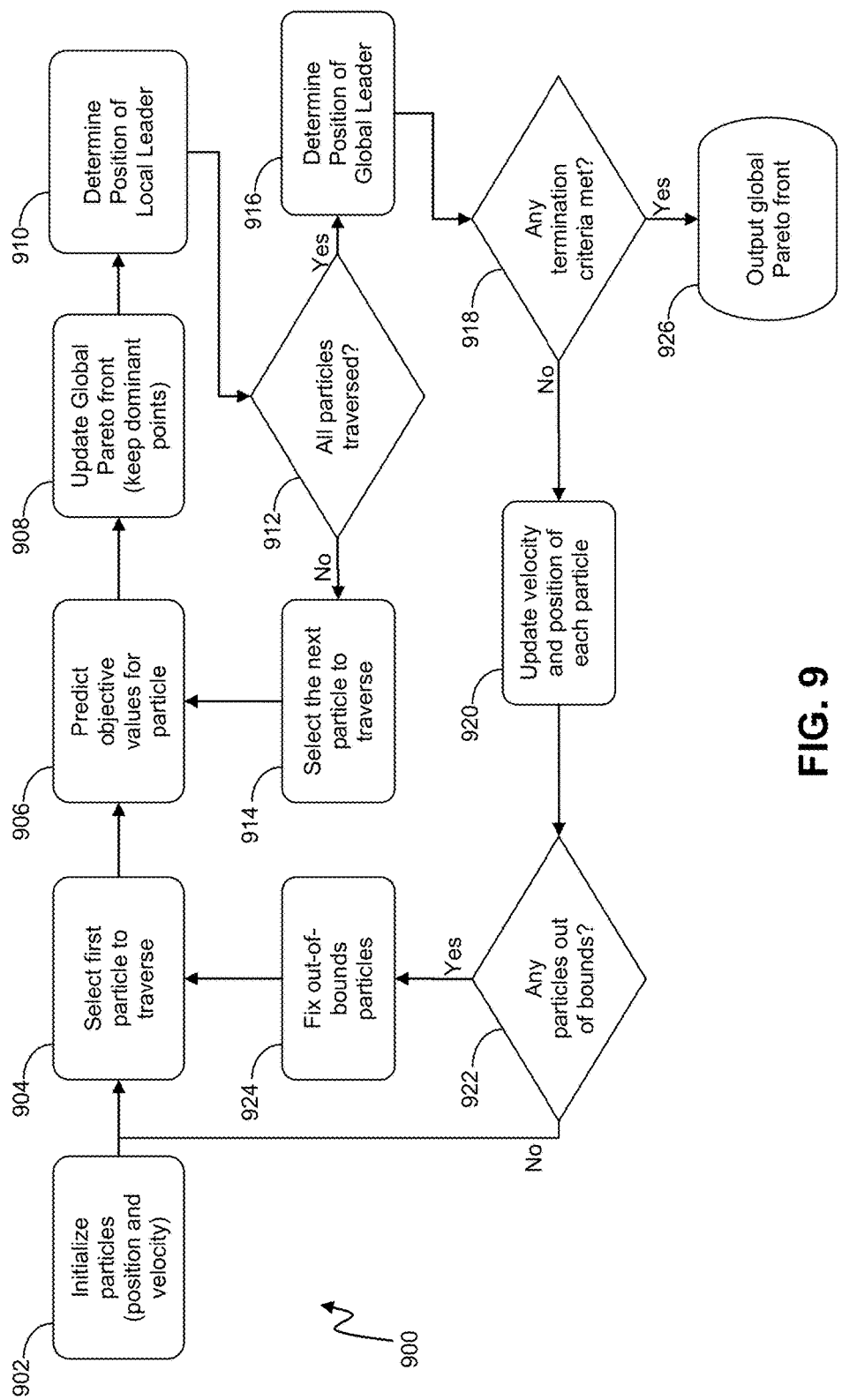
FIG. 9 is flowchart depicting a method of generating optimal configurations, according to an embodiment.

FIG. 9 is a flowchart depicting a method 900 for generation of Pareto front 806 using particle swarm optimization according to embodiments. According to method 900, each particle exhibits three simple behaviors that enable it to search through the solution space, and to communicate its findings to neighboring individuals (the swarm). The most fundamental of these behaviors is the particle's persistent and somewhat random movement through the solution space, which enables it to explore different potential solutions over time (i.e. inertia). The second behavior is the particle's tendency to move toward a point that the swarm considers to be the best so far (i.e. the "social" or "global" best). The third behavior is the particle's tendency to move towards the best point the particle itself has found (i.e. the "cognitive" best).

Similar to genetic algorithm approaches, particle swarm optimization involves the exploration of a solution space over the course of multiple "generations" in order to find optimal solutions. As depicted in FIG. 9, method 900 includes initializing the particles (including position and velocity) at 902, and then beginning at 904 selecting the first particle to traverse. For each particle, the objective values are predicted at 906. The generated global Pareto front is updated to keep dominant particles at 908.

At 910, the local leader, or "best" position is determined for the particle. In embodiments, an aggregate objective function value can be evaluated for the particle, and if the objective function value for the current iteration is better than the previous objective function value, the current position of the particle can be selected to be the local leader. In embodiments in which only Pareto dominance is considered, a local Pareto front can be maintained for the particle. In each iteration, the local Pareto front can be updated to keep the non-dominated points. The local leader can be selected randomly from the set of points on the local Pareto front.

At 912, if particles remain to be traversed, the next particle is selected at 914, which is processed beginning at 906. If, at 912, all particles have been traversed, at 916 the position of the global leader can be determined. Where aggregate objective functions are available, the global leader can be chosen by determining which of the local leader positions of the particles has the best objective function value. In embodiments, the global leader can be chosen randomly from the local leader positions of the particles, or it can be chosen at random from the positions on the global Pareto front. Where local Pareto fronts are available, the global leader can be chosen randomly from any position on a local Pareto front of any particle.

At 918, termination criteria can be evaluated. If the criteria have not been met, the position and velocity of each particle is updated at 920. Any particles that are out-of-bounds based on constraints can be detected at 922 and fixed at 924, before a new iteration of processing of the set of particles begins again at 904. The various elements of method 900 are discussed in more detail with reference to specific embodiments below.

According to embodiments, at 902, each particle can be initialized to a given position in the solution space of $x_i$, where i is the particle number and each electrode current value in vector x is within defined constraints for minimum and maximum current for each electrode. In embodiments, the current values can be constrained (assuming a cathode-leading phase) based on known current density safety limits based on the electrode size, though other constraints can of course be used. In an embodiment, 100 total particles are generated, with 68 initialized to have random current through each electrode (e.g. within 0 to −0.25 mA). The remaining particles are initialized to have exactly −0.25 mA going through only a single electrode. This so-called "multi-start initialization" approach can promote exploration of the search space.

At 902, each particle's initial velocity term (i.e. the change in current), $v_i(0)$, can further be set. In embodiments, $v_i(0)$ can be set to zero, or be set randomly or in other ways for each particle.

At 904 and 914, the particles can be traversed in any order, including numerically, or randomly, such that each particle is traversed in each generation.

At 906, various objective values can be calculated for the selected particle. In embodiments, objective values can be combined into an objective vector, and/or used as input to an objective function, as described with reference to 910 below. In an example, such as that depicted in FIGS. 8A and 8B, the objectives can include maximizing R ($\vec{x}$), the number of axons activated in a region of interest (ROI), minimizing S ($\vec{x}$), the number of axons activated in a region of avoidance (ROA), and minimizing P ($\vec{x}$), the power dissipated by the stimulator. As depicted and described with reference to FIGS. 8C and 8D above, however, many more objectives can be used, including multiple regions and/or pathways of both interest and avoidance. Each of these objectives can reflect a desired clinical outcome, in which robust therapy is delivered with little to no side effects and with low power consumption. By way of example, the objective values R ($\vec{x}$), S ($\vec{x}$), and P ($\vec{x}$), as used in the embodiment of FIGS. 8A and 8B can be calculated as discussed below.

In embodiments, the MAF and MAFT values discussed above can be used to estimate the number of axons activated in a ROI and the number of axons activated in a ROA. These threshold-based functions can be described by the following example formulas (though other formulas can be used):

$$R(\vec{x})\sum_{i=1}^{U} H(\max(C_{ROI,i}\vec{x}) - \alpha)$$

-continued $$S(\vec{x})\sum_{j=1}^{V} H(\max(C_{ROA,j}\vec{x}) - \alpha)$$

where x is the vector corresponding to the current through each electrode, $C_{ROI,i}$ and $C_{ROA,j}$ are the C matrices for ROI axon i and ROA axon j, respectively, H(●) is the Heaviside function, and α is the MAFT value.

Power output in mA² (not scaled by impedance) can be estimated using the following formula, as an example:

$$P(\vec{x})\sum_{k=1}^{m} (x_k^2),$$

where m is the number of electrodes

At 908, the global Pareto front can be updated so as to keep particle positions that are known, at the current iteration, to be Pareto optimal, and to remove particle positions that are known, at the current iteration, to be Pareto dominated. In embodiments, a position can be considered to be Pareto dominated if there is at least one other position that has at least one better objective value and no worse objective values. In embodiments, a position can be considered to be Pareto optimal (or dominant) if no positions exist that show at least one improved objective value and no worse objective values. Each iteration of method 900 gradually improves and refines the global Pareto front estimate.

At 910, the local leader, or "best" position is determined for the particle. This can be chosen based on an aggregate objective function, or purely Pareto dominance. In embodiments the objective function can be evaluated for the current particle, given the objective values for the particle calculated at 906. In embodiments, where the goals are to maximize R ($\vec{x}$), minimize S ($\vec{x}$), and minimize P ($\vec{x}$) the objective function value, J can be calculated, such as:

$$J(\vec{x}) = -R(\vec{x}) + S(\vec{x}) + P(\vec{x})$$

If the objective function value of the particle is less (better) than the current particle-specific best, the particle-specific best position (or local leader) is updated to the current particle position. Those of ordinary skill in the art will appreciate that other calculations of objective function values or determinations of the "best" values can be used.

In addition to linear aggregation-based approaches, there are also a number of more complex Pareto dominance-based methods that may yield more efficient Pareto front estimates (e.g. in fewer generations or with fewer particles). These Pareto dominance-based approaches rely on selecting non-dominated "leader" solutions to guide the algorithm. In embodiments using Pareto dominance-based methods, each particle can maintain an individual Pareto front comprising non-dominated positions that the particle has visited, while also contributing to the global Pareto front. The local leader position can be determined as a random point along the local Pareto front., thus promoting additional exploration and expansion of the Pareto front.

Also important to particle swarm optimization algorithms in general is the topological network of connections amongst particles and neighborhoods, which govern the convergence behavior of the algorithm. In embodiments, all particles are operably coupled to one another such that all particles in the swarm are directly informed of the global best solution at each iteration. Using such a global network enables the swarm to converge more rapidly than using a local network (e.g. ring, tree, wheel, von Neumann networks), since a locally connected network is slower to propagate the information of the global best solution. The global network's faster convergence, however, may be undesirable if it leads to premature convergence on local optima. Therefore, in embodiments a local neighborhood approach may be used to improve the diversity of exploration and consistency of the Pareto front estimates.

When all particles are traversed at 912, the global leader position can be determined at 916. In embodiments in which aggregate objective function values are available, the global leader position can be the local leader position with the best objective function value. In embodiments, the global leader position can be selected at random from the local leader positions, or from the local Pareto fronts. In embodiments, the global leader position can be selected at random from points on the global Pareto front.

Termination criteria can be checked at 918. In embodiments termination criteria can include: convergence, stalling, and/or reaching the generation limit. The criteria for convergence, stalling, and generation limits can be tuned by trial and error. In embodiments, the particles can be considered to be converged if the particles' currents are close to each other in at least a minimum number of the total electrodes, measured by a given electrode having a standard deviation less than some amount across all particles. In an example embodiment, a very strict convergence criterion can be used such that convergence is found if 30 out of 32 electrodes have a standard deviation less than 0.004 mA (<1% of max current) across all particles.

In addition, in embodiments, particles can be considered to be stalled if the objective function score (if available) does not improve for a certain number of consecutive generations. In an example embodiment, stalling can be found after 100 consecutive generations without improvement.

In embodiments, the generation limit can be any number of generations. In an example embodiment, 200 generations is the limit, as empirical data finds this to enable sufficient iterations for convergent runs to terminate while also enabling non-convergent runs to explore the solution space and improve Pareto front estimates.

If any of the termination criteria are met at 918, method 900 terminates and the estimated Pareto front 806 is reported at 926. Those of ordinary skill in the art will appreciate that other termination criteria may be used, and the specific values provided for determine convergence, stalling, or generation limit above are merely examples and other values can be substituted as appropriate. Furthermore, in embodiments using Pareto-dominance based approaches instead of combining with a linear aggregate objective function, the stalling and convergence criteria can either be omitted or redefined, since no single value (such as the objective function value) is used for comparing across particles. The maximum number of generations can be the primary termination criteria for such embodiments.

If none of the termination criteria are met at 918, the velocity and position of each particle is updated at 920. In embodiments, a particle's position in the solution space at a given time can be described as follows:

$$x_i(t+1) = x_i(t) + v_i(t+1)$$

where x is the position (i.e. the vector of currents for each electrode), i is the particle number, t is iteration, and v is the "velocity" term (i.e. the vector of changes in current for each electrode).

In embodiments, the three simple behaviors of the particle are included in this velocity term by three components: inertial, social, and cognitive. Hence, velocity is defined as:

$$v_{ij}(t+1) = w \cdot v_{ij}(t) + c_1 \cdot r_{1ij}(t) \cdot [y_{ij}(t) - x_{ij}(t)] + c_2 \cdot r_{2ij}(t) \cdot [\hat{y}_j(t) - x_{ij}(t)]$$

where j is the electrode number, w is the inertial component, $c_1$ is the cognitive component, $c_2$ is the social component, y is the position of the local leader as of iteration t, and $\hat{y}$ is the position of the global leader as of iteration t. Meanwhile, $r_{1ij}$ and $r_{2ij}$ are additional weighting factors that allow for randomness, which can promote exploration. In embodiments $r_{1ij}$ can be randomly distributed between 0 and 1 (inclusive), while $r_{2ij}$ can be set to 1 for all i and j. As such, the random component of motion can be solely due to the cognitive component. In embodiments, social component $c_2$ can be chosen to be low relative to cognitive component $c_1$ in order to promote exploration or to produce lower J values.

In embodiments, the inertial component w can be defined as follows:

$$w(t) = -\frac{w(0) - w(n)}{n} t + w(0)$$

where n is the maximum number of iterations as discussed above. In embodiments, w can be set such that it decreases linearly from 0.9 to 0.4 in order to promote initial exploration followed by a tendency to converge toward the end.

The formulas provided above for determining particle position, velocity, and inertia are examples according to certain embodiments. Those of ordinary skill in the art will appreciate that other formulas can be employed.

At 922, all particles are checked to ensure that they are not out of bounds, based on one or more bounding criteria. In embodiments, the bounding criteria can include the minimum and maximum current constraints (such as −0.5 mA to 0 mA, in an embodiment). At 924, out of bounds particles can be fixed by modifying the velocity and current for each electrode that would be outside of the constraints. For example, if after 920, electrode e in particle p has a current that is outside of the constraints, then $v_{pe}(t)$ can be set to 0, and the electrode current can be set equal to the maximum current (if the current was too high) or the minimum current (if the current was too low). Additional and alternative bounding criteria can be used.

After checking at 922 and fixing at 924, a new iteration is begun at 904 and the particles are traversed again.

User interface engine 612 can present the set of solutions in the generated Pareto front 806 to the user for comparison at 412. In embodiments, user interface engine 612 can present Pareto front 806 as a list of electrode configurations, or more intuitively, user interface engine 612 can present a visualization of Pareto front 806 in the optimization problem space as depicted in FIG. 8A. User interface engine 612 can enable a user to select one or more points on Pareto front 806 in order to view more detailed information (for example, as a color-coded array of values as in FIG. 8B), and/or to select a particular point as the electrode configuration for stimulation settings 530 to be set as device programming at 414.

User interface engine 612 can enable a user to determine the set of objectives of interest. User interface engine 612 can, in addition, present a list of preprogrammed objectives to the user. User interface engine 612 can also enable the user to define arbitrary objective functions.

In embodiments, user interface engine 612 can modify the display of optimization problem solution space 800 as necessary in order to efficiently display Pareto front 806 based on the chosen objectives. For example, optimization problem solution space 800 is depicted in a perspective view approximating three dimensions because three objectives have been chosen. In embodiments, where only two objectives are chosen, optimization problem solution space 800 may be depicted as a two dimensional graph, with Pareto front 806 shown as a curve. Similarly, if more than three objectives are chosen, user interface engine 612 may collapse the many dimensions into three for visualization, or alternatively use color, movement, or other indicators in order to provide additional dimensions of information to the user.

In embodiments, in order to facilitate multi-dimensional visualization and input, user interface engine 612 may provide three-dimensional renderings of optimization problem solution space 800 suitable for viewing through 3D viewers such as Google Cardboard, Oculus, Samsung Gear, or others. User interface engine 612 may also use sound, haptic (touch) feedback, or other input and output methods in order to enable the user to view and select stimulation settings in 3D.

In embodiments, additional objectives can include maximizing electrode configurations based on functional data provided by sensing capabilities of DBS leads such as 102 or 202 and pulse generator 108. Sensing capabilities of pulse generator 108 can be provided by a sensing engine, in embodiments. In embodiments, a DBS lead 202 and pulse generator 108 are configured such that brain activity, for example local field potential (LFP) beta activity at 20 Hz, can be sensed via DBSA lead 202. Those of ordinary skill in the art will appreciate that functional data such as features of beta activity sensed by an electrode can be correlated with increased likelihood of disease-related neural sources near any given electrode. Therefore, it may be desirable for clinicians to consider electrode configurations that include stimulation of more electrodes that detect certain functional signals.

FIG. 10A depicts a DBSA lead 202 implanted in a region of tissue 110, according to an embodiment. FIGS. 10B and 10C depict a color coded view of a functional signal representing peak beta power (at 20 Hz) in the LFP signals sensed at each electrode 104 (lighter-colored electrodes indicate more beta activity). As is clear from FIG. 10C, a strong beta signal was detected at electrode 23, and no beta signal was detected at electrode 17. FIG. 11 depicts graphs of the functional signals detected at electrode 23 and electrode 17, in which the peak beta activity at 20 Hz can be more clearly seen in electrode 23. This functional data can be provided as input to brain geometry engine 604 in addition to, or instead of MRI data 520 or brain atlas data 522.

Figures 12A, 12B:
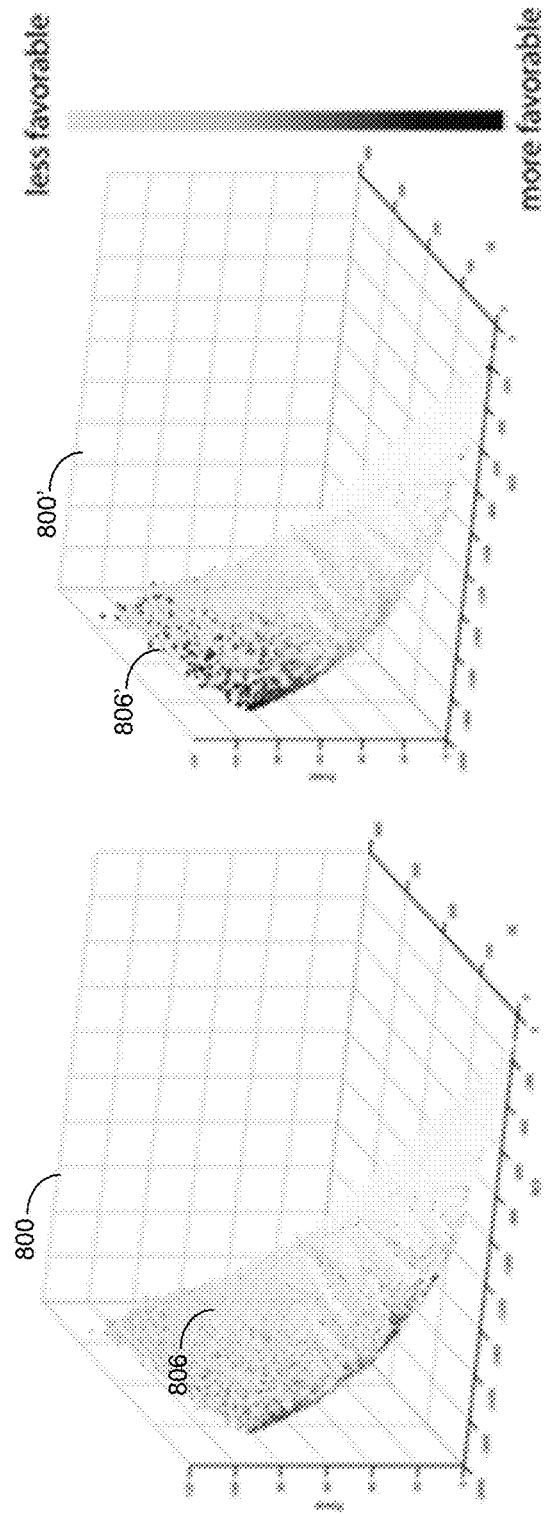
FIG. 12A is a graph depicting a visualization of a set of optimal stimulation settings, according to an embodiment.
FIG. 12B is a graph depicting a visualization of a set of optimal stimulation settings, according to an embodiment.

In embodiments, electrodes 104, and electrode configurations can be ranked based on closeness to the source of functional signals of interest. This ranking can be used as an objective value, and calculated in a manner similar to that described above with respect to the number of axons activated in the ROI and ROA, and the total power consumption. As such, this ranking can provide an additional dimension in the optimization problem space 800 and Pareto front 806. FIG. 12A depicts three-dimensional optimization problem space 800 and Pareto front 806, as discussed above. FIG. 12B, however, depicts Pareto front 806, which uses grayscale value to indicate which solutions on Pareto front 806 include electrode configurations that are closer to the source of the functional signals (darker dots) or further from the source (lighter dots). User interface engine 612 can therefore provide a visualization of Pareto front 806 with additional information based on functional data.

Those of ordinary skill in the art will appreciate that the ranking based on functional data discussed above is not limited to use with the optimization methods described herein. Functional data can also be applied as an objective in other optimization methods, including the convex optimization methods disclosed in U.S. patent application Ser. No. 15/291,628 to Xiao et al. In embodiments, functional data can be used in addition to, or instead of one or more of other objectives.

Empirical data has shown high levels of consistency, robustness, and efficiency for stimulation settings on Pareto fronts generated by method 900, such as with the following parameter values:

TABLE 1

| Parameter | Value |
| --- | --- |
| Number of Particles | 100 |
| Generation Limit | 200 |
| Stalling Generation Constant | 100 |
| Cognitive Attraction Weight, $c_1$ | 4.5 |
| Social Attraction Weight, $c_2$ | 0.2 |
| Upper Inertia | 0.9 |
| Lower Inertia | 0.4 |
| Velocity Limit | Infinite |
| Additional Cognitive Weighting, $r_{1ij}$ | [0, 1] (random) |
| Additional Social Weighting, $r_{2ij}$ | 1 |
| Lower Bound Current per Electrode | −0.5 mA |
| Upper Bound Current per Electrode | 0 mA |
| Total Bounded Current | None |

Consistency was measured by quantifying the variation in Pareto fronts across 30 independent runs as depicted in FIGS. 13A-D. In addition, each estimate was compared to a "combined" Pareto front that was constructed from all 30 Pareto front estimates. For each point Y on each of the 30 Pareto fronts, the discrepancy between Y and the closest "combined" Pareto front point was computed. As shown in FIG. 13A for five sample Pareto fronts, the fronts exhibited considerable overlap, and their respective "best" electrode configurations had in common eight out of 11-13 active electrodes (FIG. 13B). Furthermore, predicted ROI activation variation was within 2.0% across all 30 runs. A "combined" Pareto front (FIG. 13C) was constructed and its distribution of values compared to the all 30 runs (uncombined). A relatively small difference in median ROI activation (19 axons), median ROA activation (−20 axons), and median power (−4.11 mA2) was observed as depicted in FIG. 13D.

Robustness was evaluated by measuring ROI, ROA, and Power under three conditions:
(1) the existence of open electrode sites (i.e. those unusable because of very high impedances);
(2) low per electrode current limit (e.g. low battery); and (3) lead shifts by 1 mm anterior, posterior, medial, and lateral relative to the DBSA trajectory. Method 900 was able to accommodate for disabling 3 or 12 active electrodes, with ROI activation reduced by only 1.8% and 14%, respectively (FIG. 14A). Reducing the maximum per-electrode current by 50% and 80% reduced ROI activation by 5.6% and 16%, respectively (FIG. 14A). Lead displacement by 1 mm in the anterior, posterior, medial and lateral directions relative to the center location resulted in relatively small changes in ROI activation (−7.5%, −3.6%, −6.9%, +9.2%) without significantly changing ROA activation (<1% change in any direction) (FIGS. 14C-D).

Efficiency was measured as the average runtime for constructing a Pareto front and obtaining a best electrode configuration. This was assessed by running the method 900 five times on a PC with eight cores, 64-bit operating system, 24.0 GB RAM, and an Intel Core i7 processor at 3.40 GHz. Method 900 took 3.19 seconds per generation, resulting in an average of 10.6 minutes per run. These times reflected the duration for obtaining a solution after segmentation of the brain volume, positioning of the DBSA within the volume, incorporation of axonal tract morphologies, and identification of the MAFT for the ROI and ROA.

Systems and methods using particle-swarm optimization for programming of stimulation settings have a number of advantages over other known optimization methods. For example, a clinician may decide that activation within one or more regions or pathways of avoidance above 10% is undesirable for a given patient, whereas in another case, this value can be higher or lower. Therefore, while the method 900 is an automated algorithm, the user can select and test a set of optimized solutions along the Pareto front as needed, making the overall programming process more intuitive despite the complex geometries and nontrivial electrode configurations involved.

Those of ordinary skill in the art will appreciate that while the system and methods disclosed herein have been described in relation to brain stimulation, they may be applied to other applications involving the stimulation of nervous tissue including but not limited to: spinal cord, dorsal root ganglia, cardiac tissue, vagus nerve, and/or gastro-intestinal stimulation among other neural tissue in the body.

It should be understood that the individual steps used in the methods of the present teachings may be performed in any order and/or simultaneously, so long as the teaching remains operable. Furthermore, it should be understood that the apparatus and methods of the present teachings can include any number, or all, of the described embodiments, as long as the teaching remains operable.

In one embodiment, the pulse generator 108, programmer device 502 and/or their components or subsystems can include computing devices, microprocessors, modules and other computer or computing devices, which can be any programmable device that accepts digital data as input, is configured to process the input according to instructions or algorithms, and provides results as outputs. In one embodiment, computing and other such devices discussed herein can be, comprise, contain, or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves. In one embodiment, volatile memory can include random access memory (RAM), dynamic random access memory (DRAM), or static random access memory (SRAM), for example. In one embodiment, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the disclosure.

In one embodiment, the system or components thereof can comprise or include various modules or engines, each of which is constructed, programmed, configured, or otherwise adapted to autonomously carry out a function or set of functions. The term "engine" as used herein is defined as a real-world device, component, or arrangement of components implemented using hardware, such as by an application-specific integrated circuit (ASIC) or field-10 programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A method for programming a pulse generator with a configuration for a deep brain stimulation array including one or more electrodes, the configuration including a stimulation setting for each electrode in the deep brain stimulation array, the method comprising:
   identifying one or more grid points representing a target tissue to be activated by stimulation through the one or more electrodes;
   identifying one or more objective values to be balanced, the objective values being calculable based on the one or more grid points and a configuration;
   generating one or more configurations, such that each configuration is Pareto optimal in terms of the objective values calculated based on the one or more grid points and the configuration;
   presenting the one or more configurations to a user;
   receiving from the user a selected one of the one or more configurations; and
   providing, to a pulse generator capable of delivering therapy via each of the one or more electrodes, the selected configuration.

2. The method of claim 1, wherein generating the one or more configurations comprises:
   in a memory, storing data elements representing one or more particles, each particle comprising a current configuration and a local leader configuration;
   in the memory, allocating storage space for a set of dominant particles;
   iteratively:
      calculating the one or more objective values for each of the one or more particles based on the one or more grid points and the current configuration for the particle,
      updating the set of dominant particles to contain only Pareto dominant particles, wherein a particle is Pareto dominant if there exist no other particles having at least one objective value that is better than a corresponding objective value of the particle and having no objective values that are worse than the corresponding objective values of the particle,
      determining the local leader configuration for each particle,
      determining a global leader configuration, and
      modifying the current configuration for each particle based on the local leader configuration for the particle and the global leader configuration until a termination criterion has been met; and
   providing the configurations of each particle in the set of dominant particles.

3. The method of claim 2, wherein the termination criterion is selected from the group consisting of: a maximum number of iterations, convergence, and stalling.

4. The method of claim 2, wherein modifying the current configuration for each particle comprises modifying the current configuration for the particle based on an inertial component, a cognitive component, and a social component.

5. The method of claim 4, wherein:
   each particle further comprises a set of previous configurations for the particle;
   the inertial component is based on the current configuration for the particle and the set of previous configurations for the particle;
   the cognitive component is based on the local leader configuration for the particle; and
   the social component is based on the global leader configuration.

6. The method of claim 4, wherein modifying the current configuration for each particle further comprises modifying the current configuration for each particle based on one or more weighting factors.

7. The method of claim 6, wherein the functional data comprises spectral features of local field potential activity collected adjacent or distal to the stimulated electrodes.

8. The method of claim 2, further comprising:
   identifying an objective function calculable based on the one or more objective values;
   wherein determining the local leader configuration for each particle comprises
      calculating the objective function for the current configuration for the particle, and
      identifying the current configuration for the particle as the local leader configuration for the particle if the objective function for the current configuration is better than the objective function for a previous local leader configuration; and
   wherein determining the global leader configuration comprises identifying the particle having the local leader configuration with the best objective function.

9. The method of claim 2, wherein each particle further comprises a local dominant set of configurations;
   wherein calculating the one or more objective values for each of the one or more particles further comprises updating the local dominant set of configurations by adding the current configuration to the local dominant set of configurations if there exist no other configurations in the local dominant set of configurations having at least one objective value that is better than the corresponding objective value of the current configuration and having no objective values that are worse than the corresponding objective values of the current configuration, and removing any configuration from the local dominant set of configurations that have at least one objective value that is worse than the corresponding objective value of the current configuration and no objective values that are better than the corresponding objective values of the current configuration;

wherein determining the local leader configuration for each of the one or more particles comprises choosing a random configuration from the local dominant set of configurations; and wherein determining the global leader configuration comprises choosing the local leader configuration for a random particle.

10. The method of claim 1 wherein the objective values are selected from the group consisting of:
a number of axons activated in one or more regions of interest,
a number of axons activated in one or more pathways of interest,
a number of axons activated in one or more regions of avoidance,
a number of axons activated in one or more pathways of avoidance, and
a total power required for stimulation.

11. The method of claim 1, further comprising:
receiving functional data related to the proximity of brain activity to each of the one or more electrodes;
wherein at least one of the objective values includes the proximity of brain activity to each of the electrodes activated by the configuration.

12. A system for stimulation of brain tissue via an implantable deep brain stimulation array including one or more electrodes, the system comprising:
a pulse generator programming device comprising:
a brain geometry engine configured to generate, from brain geometry data, one or more grid points representing a target tissue to be activated;
a discretization engine configured to determine and estimated modulation at each of the one or more grid points for a given configuration based on lead geometry data;
an optimization engine configured to generate one or more configurations, each configuration including a stimulation setting for each electrode, by
identifying one or more objective values to be balanced, the objective values being calculable based on the one or more grid points and a configuration; and generating the one or more configurations such that each configuration is Pareto optimal in terms of the objective values calculated based on the one or more grid points and the configuration;
a user interface configured to present the generated one or configurations to the user and receive a selected one of the one or more configurations; and
a pulse generator in communication with the pulse generator programming device and electrically coupled to the implantable deep brain stimulation array and comprising a memory configured to store the selected configuration and a stimulation engine configured to deliver therapeutic pulses to each of the one or more electrodes according to the stimulation setting for the electrode of the configuration.

13. The system of claim 12, wherein the optimization engine comprises:
a memory adapted to store data elements representing one or more particles, each particle comprising a current configuration and a local leader configuration, and data elements representing a set of dominant particles; and
wherein the optimization engine is configured to generate the one or more configurations by iteratively:
calculating the one or more objective values for each of the one or more particles based on the one or more grid points and the current configuration for the particle,
updating the set of dominant particles to contain only Pareto dominant particles, wherein a particle is Pareto dominant if there exist no other particles having at least one objective value that is better than the corresponding objective value of the particle and having no objective values that are worse than the corresponding objective values of the particle,
determining the local leader configuration for each particle,
determining a global leader configuration, and
modifying the current configuration for each particle based on the local leader configuration for the particle and the global leader configuration until a termination criterion has been met;
wherein the one or more configurations are the configurations of each particle in the set of dominant particles.

14. The system of claim 13, wherein the optimization engine is further configured to:
identifying an objective function calculable based on the one or more objective values,
wherein determining the local leader configuration for each particle comprises:
calculating the objective function for the current configuration for the particle, and
identifying the current configuration for the particle as the local leader configuration for the particle if the objective function for the current configuration is better than the objective function for a previous local leader configuration, and
wherein determining the global leader configuration comprises identifying the particle having the local leader configuration with the best objective function.

15. The system of claim 13, wherein each particle further comprises a local dominant set of configurations;
wherein calculating the one or more objective values for each of the one or more particles further comprises updating the local dominant set of configurations by:
adding the current configuration to the local dominant set of configurations if there exist no other configurations in the local dominant set of configurations having at least one objective value that is better than the corresponding objective value of the current configuration and having no objective values that are worse than the corresponding objective values of the current configuration, and
removing any configuration from the local dominant set of configurations that have at least one objective value that is worse than the corresponding objective value of the current configuration and no objective values that are better than the corresponding objective values of the current configuration,
wherein determining the local leader configuration for each of the one or more particles comprises choosing a random configuration from the local dominant set of configurations, and wherein determining the global leader configuration comprises choosing the local leader configuration for a random particle.

16. The system of claim 13, wherein modifying the current configuration for each particle comprises modifying the current configuration for the particle based on an inertial component, a cognitive component, and a social component.

17. The system of claim 16, wherein:
 each particle further comprises a set of previous configurations for the particle;
 the inertial component is based on the current configuration for the particle and the set of previous configurations for the particle;
 the inertial component is based on the current configuration for the particle and any previous configurations for the particle;
 the cognitive component is based on the local leader configuration for the particle; and
 the social component is based on the global leader configuration.

18. The system of claim 16, wherein modifying the current configuration for each particle further comprises modifying the current configuration based on one or more weighting factors.

19. The system of claim 12, wherein the pulse generator further comprises:
 a sensing engine configured to detect functional data related to the proximity of each of the one or more electrodes to brain activity;
 and wherein at least one of the objective values includes the distance of brain activity to each of the electrodes activated by the configuration.

20. The system of claim 19, wherein the functional data comprises spectral features of local field potential activity collected adjacent or distal to the stimulated electrodes.

* * * * *